United States Patent
Barrus et al.

(10) Patent No.: US 10,722,276 B2
(45) Date of Patent: Jul. 28, 2020

(54) TAPER LOCK HOOK

(71) Applicant: K2M, Inc., Leesburg, VA (US)

(72) Inventors: Michael Barrus, Redondo Beach, CA (US); Scott Jones, McMurray, PA (US); Brandon Moore, Leesburg, VA (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/169,153

(22) Filed: Oct. 24, 2018

(65) Prior Publication Data

US 2019/0053830 A1 Feb. 21, 2019

Related U.S. Application Data

(62) Division of application No. 14/211,573, filed on Mar. 14, 2014, now abandoned.

(60) Provisional application No. 61/781,813, filed on Mar. 14, 2013.

(51) Int. Cl.
*A61B 17/70* (2006.01)

(52) U.S. Cl.
CPC ...... *A61B 17/7056* (2013.01); *A61B 17/7032* (2013.01)

(58) Field of Classification Search
CPC ............ A61B 17/7034; A61B 17/7035; A61B 17/7037; A61B 17/7046; A61B 17/8685; A61B 17/7032
See application file for complete search history.

(56) References Cited

U.S. PATENT DOCUMENTS

| | | | |
|---|---|---|---|
| 4,805,602 | A | 2/1989 | Puno et al. |
| 4,946,458 | A | 8/1990 | Harms et al. |
| 4,950,269 | A | 8/1990 | Gaines, Jr. |
| 4,987,892 | A | 1/1991 | Krag et al. |
| 5,005,562 | A | 4/1991 | Cotrel |
| 5,176,680 | A | 1/1993 | Vignaud et al. |
| 5,190,543 | A | 3/1993 | Schlapfer |
| 5,207,678 | A | 5/1993 | Harms et al. |
| 5,217,497 | A | 6/1993 | Mehdian |

(Continued)

FOREIGN PATENT DOCUMENTS

| | | |
|---|---|---|
| JP | 2005246061 A | 9/2005 |
| JP | 2007167642 A | 7/2007 |
| WO | 2009091689 A1 | 7/2009 |

OTHER PUBLICATIONS

International Search Report issued in International Application No. PCT/US08/80682 dated Dec. 11, 2008.

*Primary Examiner* — Julianna N Harvey
(74) *Attorney, Agent, or Firm* — Lerner, David, Littenberg, Krumholz & Mentlik, LLP

(57) ABSTRACT

A spinal hook includes a hook member, an inner collet, and an outer portion. The hook member includes a head portion and a blade portion. The inner collet includes a base portion configured to rotatably engage the head portion and a pair of engaging portions defining a slot configured to receive a connecting rod therein. The outer portion is movable relative to the inner collet between a locked position in which the outer portion causes the pair of engaging portions to move toward each other and an unlocked position in which the outer portion causes the pair of engaging portions to be spread apart to facilitate insertion or removal of the connecting rod.

17 Claims, 20 Drawing Sheets

(56) References Cited

U.S. PATENT DOCUMENTS

| | | |
|---|---|---|
| 5,257,993 A | 11/1993 | Asher et al. |
| 5,261,909 A | 11/1993 | Sutterlin et al. |
| 5,261,912 A | 11/1993 | Frigg |
| 5,263,954 A | 11/1993 | Schlapfer et al. |
| 5,306,275 A | 4/1994 | Bryan |
| 5,346,493 A | 9/1994 | Stahurski et al. |
| 5,360,431 A | 11/1994 | Puno et al. |
| 5,368,594 A | 11/1994 | Martin et al. |
| 5,374,267 A | 12/1994 | Siegal |
| 5,397,363 A | 3/1995 | Gelbard |
| 5,415,659 A | 5/1995 | Lee et al. |
| 5,437,669 A | 8/1995 | Yuan et al. |
| 5,443,467 A | 8/1995 | Biedermann et al. |
| 5,446,237 A | 8/1995 | Abe et al. |
| 5,476,464 A | 12/1995 | Metz-Stavenhagen et al. |
| 5,487,742 A | 1/1996 | Cotrel |
| 5,527,314 A | 6/1996 | Brumfield et al. |
| 5,534,001 A | 7/1996 | Schlapfer et al. |
| 5,542,946 A | 8/1996 | Logroscino et al. |
| 5,575,792 A | 11/1996 | Errico et al. |
| 5,578,033 A | 11/1996 | Errico et al. |
| 5,584,832 A | 12/1996 | Schlapfer |
| 5,609,592 A | 3/1997 | Brumfield et al. |
| 5,609,593 A | 3/1997 | Errico et al. |
| 5,609,594 A | 3/1997 | Errico et al. |
| 5,620,444 A | 4/1997 | Assaker |
| 5,630,816 A | 5/1997 | Kambin |
| 5,630,817 A | 5/1997 | Rokegem et al. |
| 5,676,665 A | 10/1997 | Bryan |
| 5,683,392 A | 11/1997 | Richelsoph et al. |
| 5,688,273 A | 11/1997 | Errico et al. |
| 5,688,274 A | 11/1997 | Errico et al. |
| 5,725,527 A | 3/1998 | Biedermann et al. |
| 5,733,285 A | 3/1998 | Errico et al. |
| 5,738,685 A | 4/1998 | Halm et al. |
| 5,741,254 A | 4/1998 | Henry et al. |
| 5,782,957 A | 7/1998 | Rinker et al. |
| 5,810,816 A | 9/1998 | Roussouly et al. |
| 5,810,817 A | 9/1998 | Roussouly et al. |
| 5,810,818 A | 9/1998 | Errico et al. |
| 5,885,286 A | 3/1999 | Sherman et al. |
| 5,888,221 A | 3/1999 | Gelbard |
| 5,928,232 A | 7/1999 | Howland et al. |
| 5,964,760 A | 10/1999 | Richelsoph |
| 5,989,250 A | 11/1999 | Wagner et al. |
| 6,010,503 A | 1/2000 | Richelsoph et al. |
| 6,074,391 A | 6/2000 | Metz-Stavenhagen et al. |
| 6,077,263 A | 6/2000 | Ameil et al. |
| 6,086,588 A | 7/2000 | Ameil et al. |
| 6,110,172 A | 8/2000 | Jackson |
| 6,132,430 A | 10/2000 | Wagner |
| 6,132,434 A | 10/2000 | Sherman et al. |
| 6,254,602 B1 | 7/2001 | Justis |
| 6,273,888 B1 | 8/2001 | Justis |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,322,562 B1 | 11/2001 | Wolter |
| 6,352,537 B1 | 3/2002 | Strnad |
| RE37,665 E | 4/2002 | Ralph et al. |
| 6,413,258 B1 | 7/2002 | Bernhardt, Jr. |
| 6,416,515 B1 | 7/2002 | Wagner |
| 6,440,132 B1 | 8/2002 | Jackson |
| 6,475,218 B2 | 11/2002 | Gournay et al. |
| 6,485,491 B1 | 11/2002 | Farris et al. |
| 6,554,831 B1 | 4/2003 | Rivard et al. |
| 6,562,040 B1 | 5/2003 | Wagner |
| 6,565,565 B1 | 5/2003 | Yuan et al. |
| 6,589,243 B1 | 7/2003 | Viart et al. |
| 6,595,992 B1 | 7/2003 | Wagner et al. |
| 6,613,050 B1 | 9/2003 | Wagner et al. |
| 6,626,908 B2 | 9/2003 | Cooper et al. |
| 6,641,585 B2 | 11/2003 | Sato et al. |
| 6,648,888 B1 | 11/2003 | Shluzas |
| 6,656,180 B2 | 12/2003 | Stahurski |
| 6,660,004 B2 | 12/2003 | Barker et al. |
| 6,736,820 B2 | 5/2004 | Biedermann et al. |
| 6,740,089 B2 | 5/2004 | Haider |
| 6,746,449 B2 | 6/2004 | Jones et al. |
| 6,749,361 B2 | 6/2004 | Hermann et al. |
| 6,805,716 B2 | 10/2004 | Ralph et al. |
| 6,827,719 B2 | 12/2004 | Ralph et al. |
| 6,835,196 B2 | 12/2004 | Biedermann et al. |
| 6,837,889 B2 | 1/2005 | Shluzas |
| 6,843,791 B2 | 1/2005 | Serhan |
| 6,869,433 B2 | 3/2005 | Glascott |
| 6,884,244 B1 | 4/2005 | Jackson |
| 6,893,443 B2 | 5/2005 | Frigg et al. |
| 6,896,677 B1 | 5/2005 | Lin |
| 6,911,030 B1 | 6/2005 | Vanacker et al. |
| 6,918,911 B2 | 7/2005 | Biedermann et al. |
| 6,945,972 B2 | 9/2005 | Frigg et al. |
| 6,945,975 B2 | 9/2005 | Dalton |
| 6,974,460 B2 | 12/2005 | Carbone et al. |
| RE39,035 E | 3/2006 | Finn et al. |
| RE39,089 E | 5/2006 | Ralph et al. |
| 7,087,057 B2 | 8/2006 | Konieczynski et al. |
| 7,090,674 B2 | 8/2006 | Doubler et al. |
| 7,105,029 B2 | 9/2006 | Doubler et al. |
| 7,118,303 B2 | 10/2006 | Doubler et al. |
| 7,160,300 B2 | 1/2007 | Jackson |
| 7,332,979 B2 | 2/2008 | Connell et al. |
| 7,334,961 B2 | 2/2008 | Doubler et al. |
| 7,335,201 B2 | 2/2008 | Doubler et al. |
| 7,338,490 B2 | 3/2008 | Ogilvie et al. |
| 7,445,627 B2 | 11/2008 | Hawkes et al. |
| 7,485,133 B2 | 2/2009 | Cannon et al. |
| 7,608,095 B2 | 10/2009 | Yuan et al. |
| 7,651,516 B2 | 1/2010 | Petit et al. |
| 7,658,582 B2 | 2/2010 | Doubler et al. |
| 7,674,277 B2 | 3/2010 | Burd et al. |
| 7,678,136 B2 | 3/2010 | Doubler et al. |
| 7,780,703 B2 | 8/2010 | Yuan et al. |
| 7,785,352 B2 | 8/2010 | Snyder et al. |
| 7,789,899 B2 | 9/2010 | Markworth et al. |
| 7,819,901 B2 | 10/2010 | Yuan et al. |
| 7,931,654 B2 | 4/2011 | Jones et al. |
| 7,935,133 B2 | 5/2011 | Malek |
| 7,988,694 B2 | 8/2011 | Barrus et al. |
| 8,114,092 B2 | 2/2012 | Altarac et al. |
| 8,202,299 B2 | 6/2012 | Wang et al. |
| 8,328,817 B2 | 12/2012 | Strauss |
| 8,361,122 B2 | 1/2013 | Barrus et al. |
| 8,377,101 B2 | 2/2013 | Barrus et al. |
| 8,696,717 B2 | 4/2014 | Rock et al. |
| 8,814,919 B2 | 8/2014 | Barrus et al. |
| 2002/0032443 A1 | 3/2002 | Sherman et al. |
| 2002/0143341 A1 | 10/2002 | Biedermann et al. |
| 2004/0111091 A1 | 6/2004 | Ogilvie et al. |
| 2004/0147937 A1 | 7/2004 | Dunbar et al. |
| 2004/0158247 A1 | 8/2004 | Sitiso et al. |
| 2005/0049589 A1 | 3/2005 | Jackson |
| 2005/0053423 A1 | 3/2005 | Doubler et al. |
| 2005/0080415 A1 | 4/2005 | Keyer et al. |
| 2005/0113927 A1* | 5/2005 | Malek ............... A61B 17/7008 623/17.16 |
| 2005/0137593 A1 | 6/2005 | Gray et al. |
| 2005/0149048 A1 | 7/2005 | Leport et al. |
| 2005/0203516 A1 | 9/2005 | Biedermann et al. |
| 2005/0222575 A1 | 10/2005 | Ciccone et al. |
| 2006/0084990 A1 | 4/2006 | Gournay et al. |
| 2006/0161153 A1 | 7/2006 | Hawkes et al. |
| 2006/0173456 A1 | 8/2006 | Hawkes et al. |
| 2006/0200128 A1 | 9/2006 | Mueller |
| 2006/0200132 A1 | 9/2006 | Chao et al. |
| 2006/0217715 A1 | 9/2006 | Serhan et al. |
| 2006/0235426 A1 | 10/2006 | Lim et al. |
| 2006/0271047 A1 | 11/2006 | Jackson |
| 2006/0276792 A1 | 12/2006 | Ensign et al. |
| 2007/0016189 A1 | 1/2007 | Lake et al. |
| 2007/0049931 A1 | 3/2007 | Justis et al. |
| 2007/0093817 A1 | 4/2007 | Barrus et al. |
| 2007/0162010 A1 | 7/2007 | Chao et al. |
| 2007/0167954 A1 | 7/2007 | Sicvol et al. |

(56) References Cited

U.S. PATENT DOCUMENTS

| | | |
|---|---|---|
| 2007/0282337 A1 | 12/2007 | Garamszegi |
| 2007/0286703 A1 | 12/2007 | Doubler et al. |
| 2008/0132957 A1 | 6/2008 | Matthis et al. |
| 2008/0137933 A1 | 6/2008 | Kim |
| 2008/0243193 A1 | 10/2008 | Ensign et al. |
| 2008/0306488 A1 | 12/2008 | Altarac et al. |
| 2009/0018593 A1 | 1/2009 | Barrus et al. |
| 2009/0105769 A1* | 4/2009 | Rock ................ A61B 17/7032 606/308 |
| 2009/0234395 A1 | 9/2009 | Hoffman et al. |
| 2009/0318970 A1 | 12/2009 | Butler et al. |
| 2010/0222822 A1 | 9/2010 | Farris et al. |
| 2010/0274291 A1 | 10/2010 | McClellan, III et al. |
| 2010/0305616 A1 | 12/2010 | Carbone |
| 2013/0013003 A1 | 1/2013 | Carbone et al. |

* cited by examiner

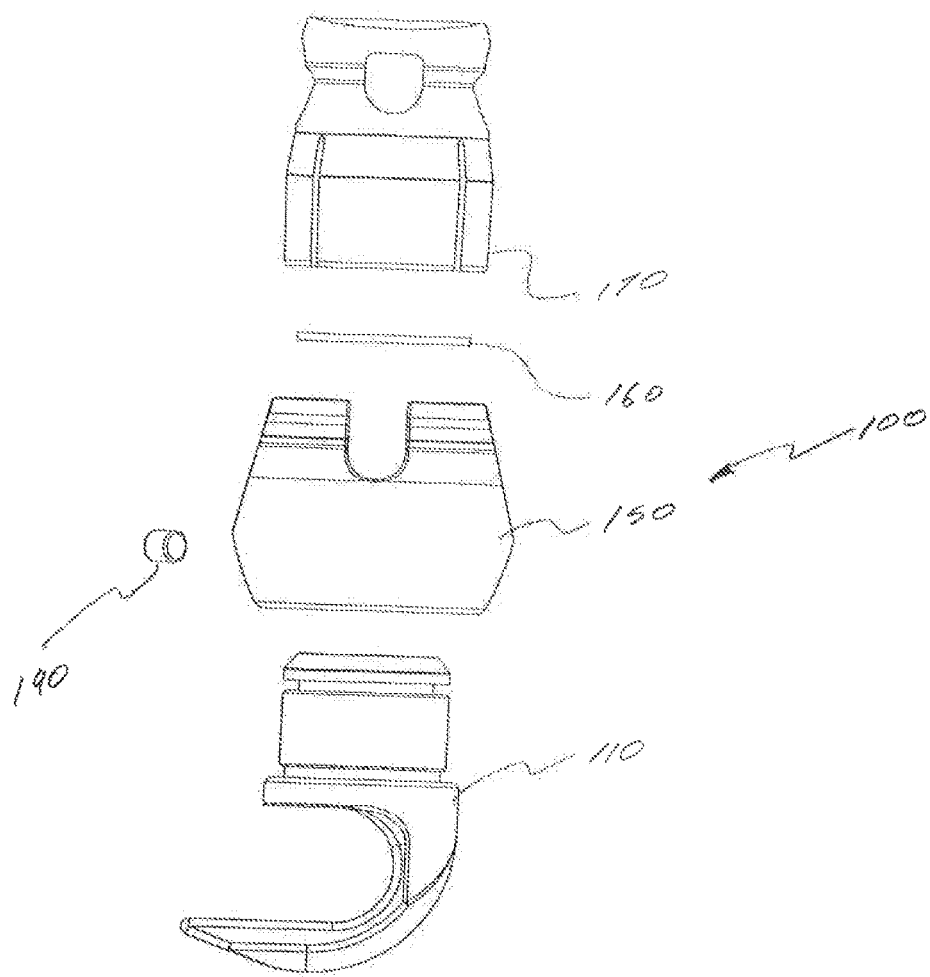
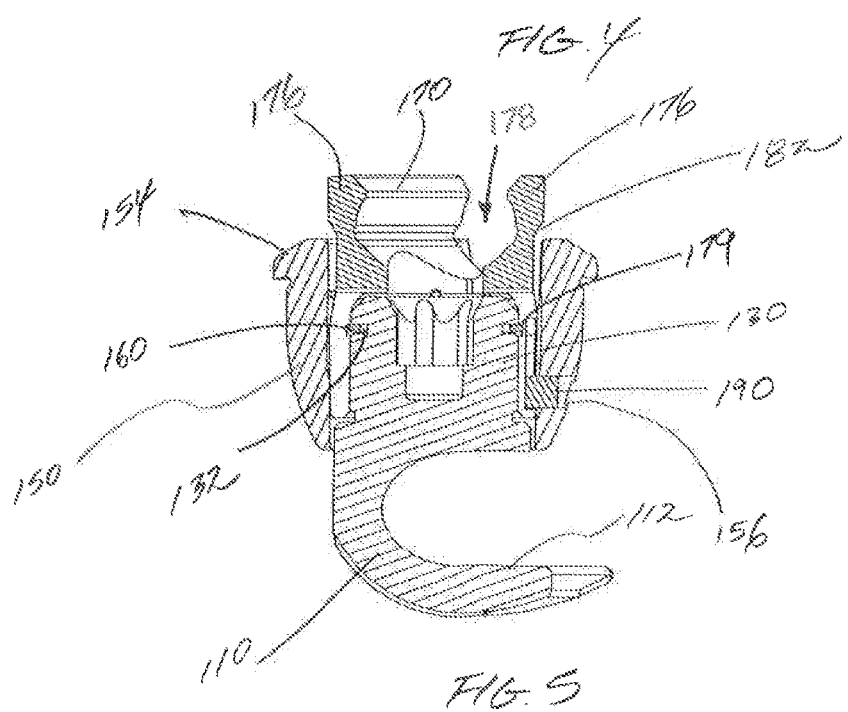

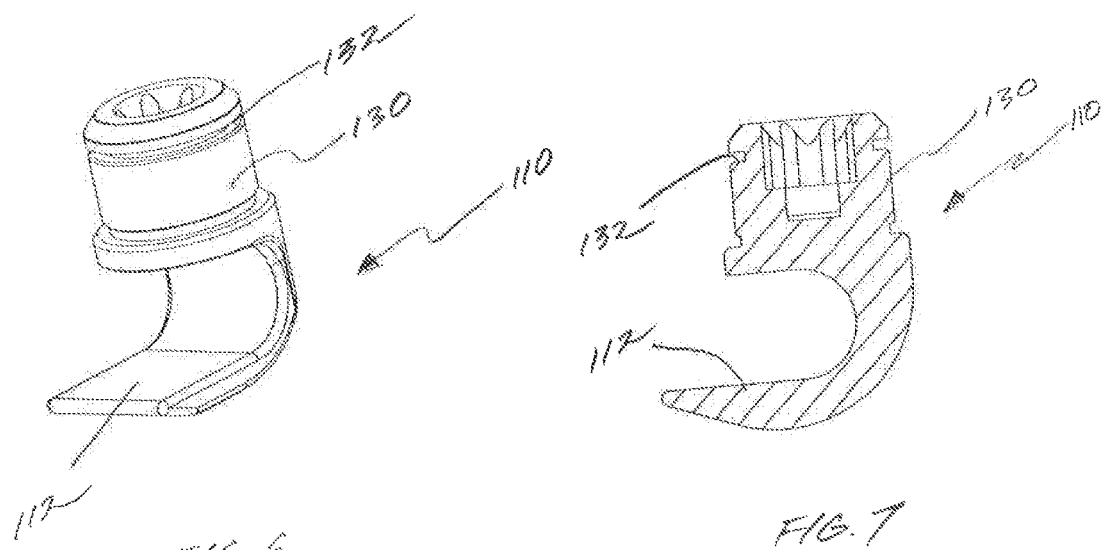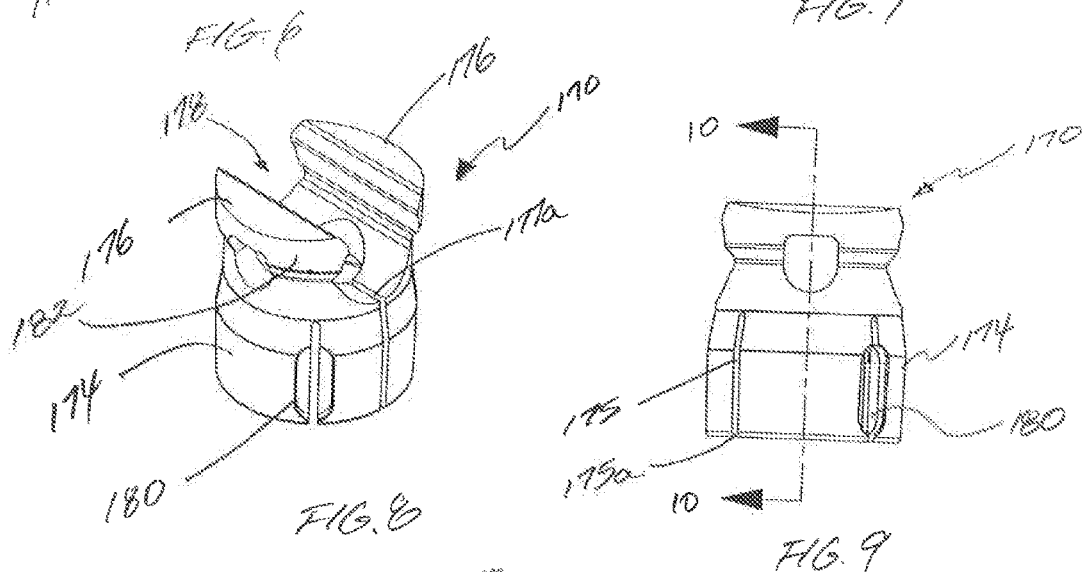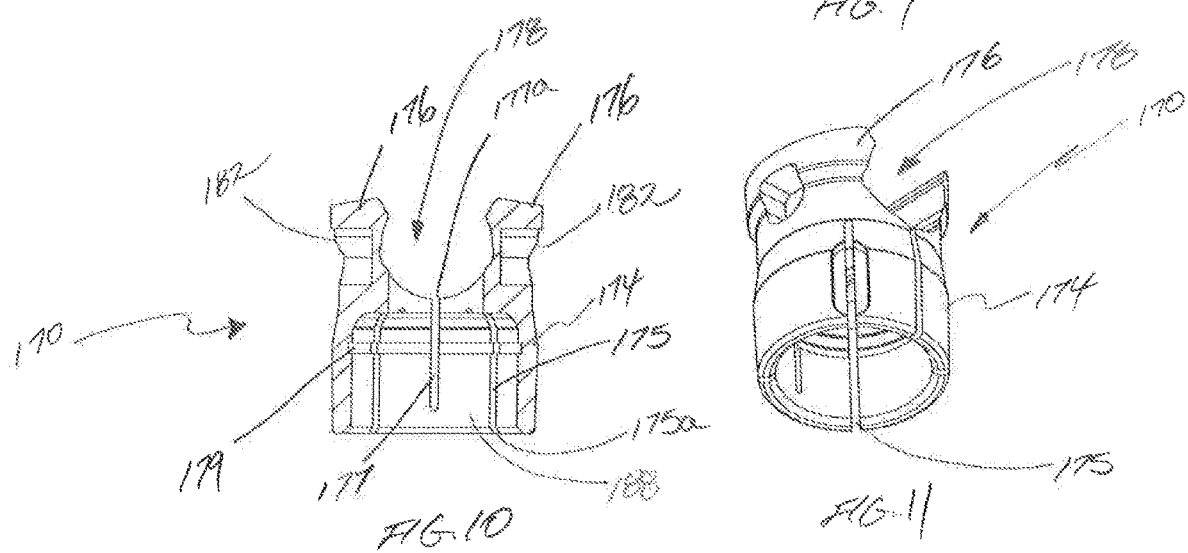

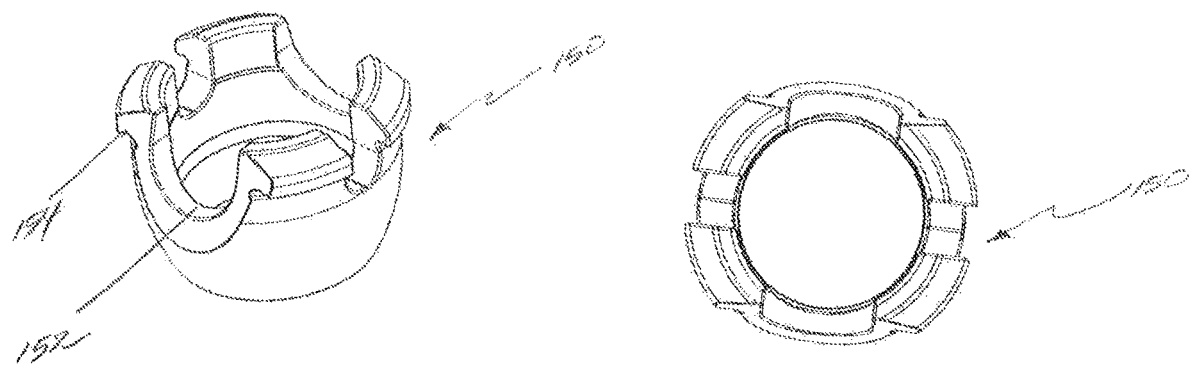
FIG. 12
FIG. 13
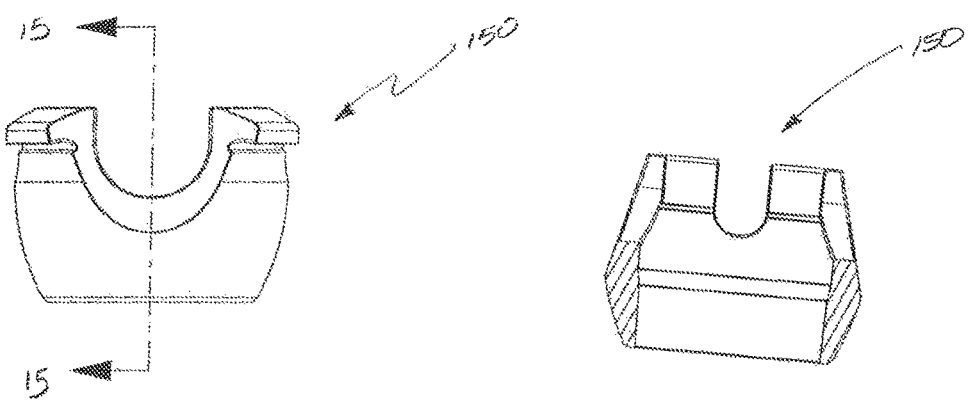
FIG. 14
FIG. 15
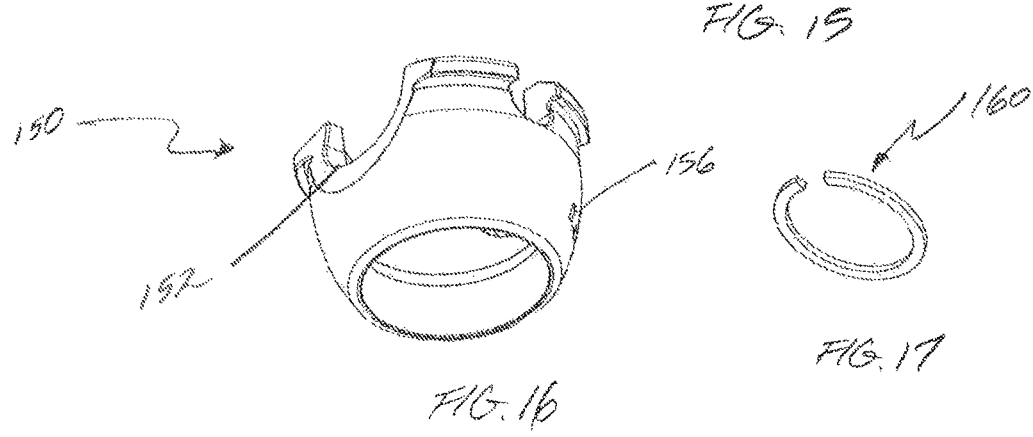
FIG. 16
FIG. 17

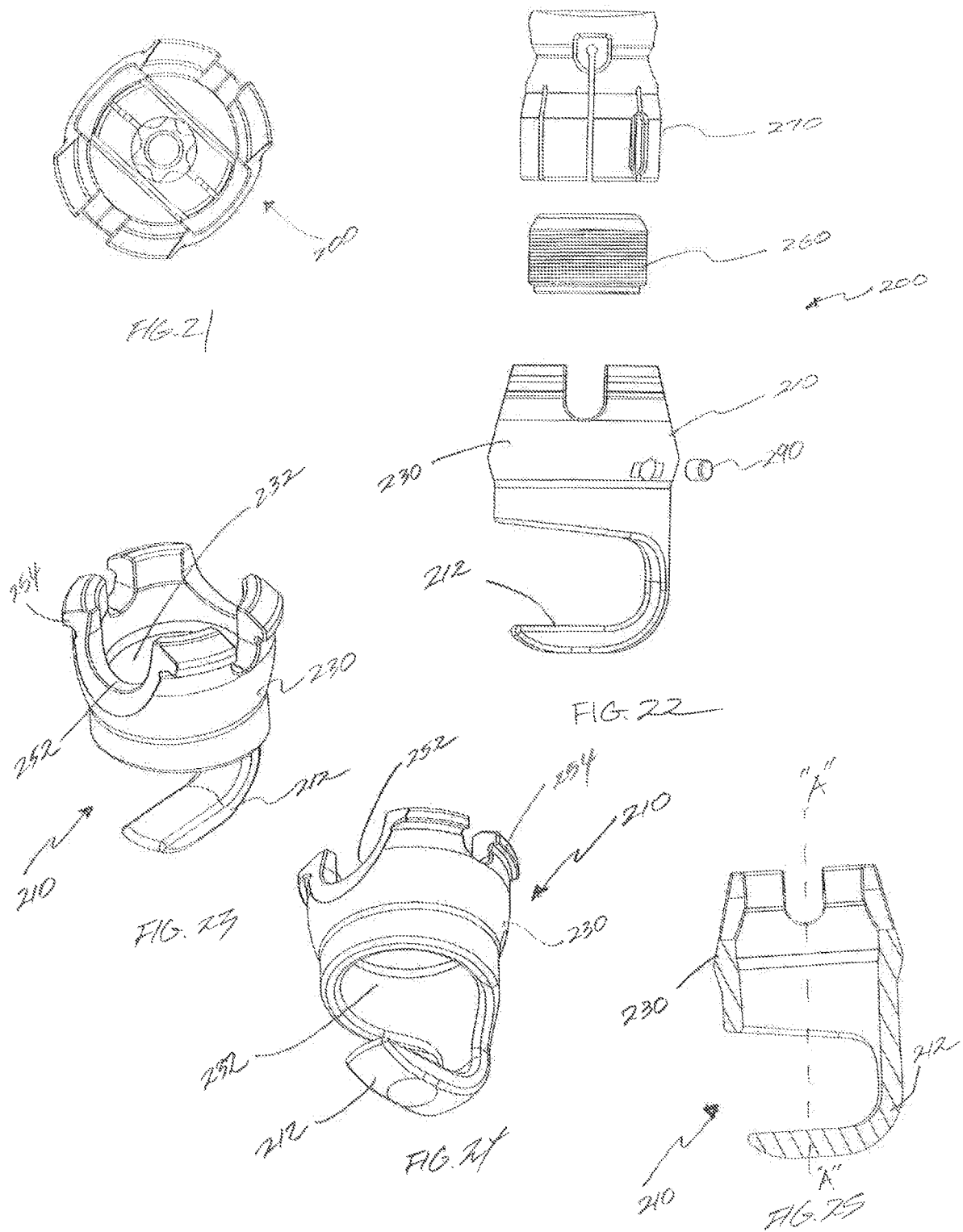

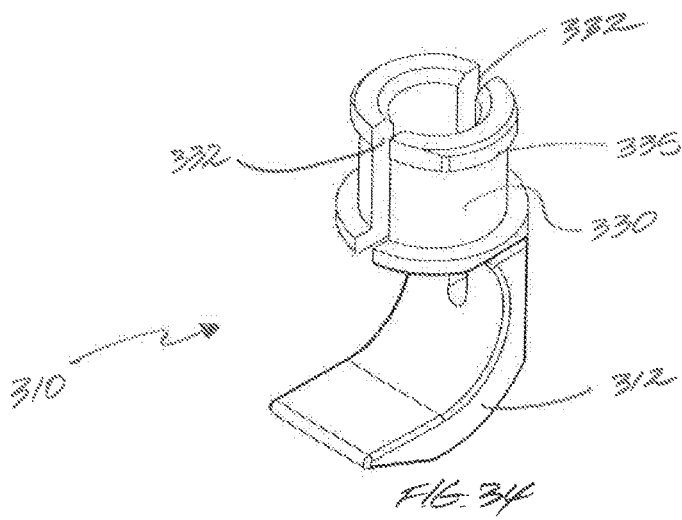
FIG. 34
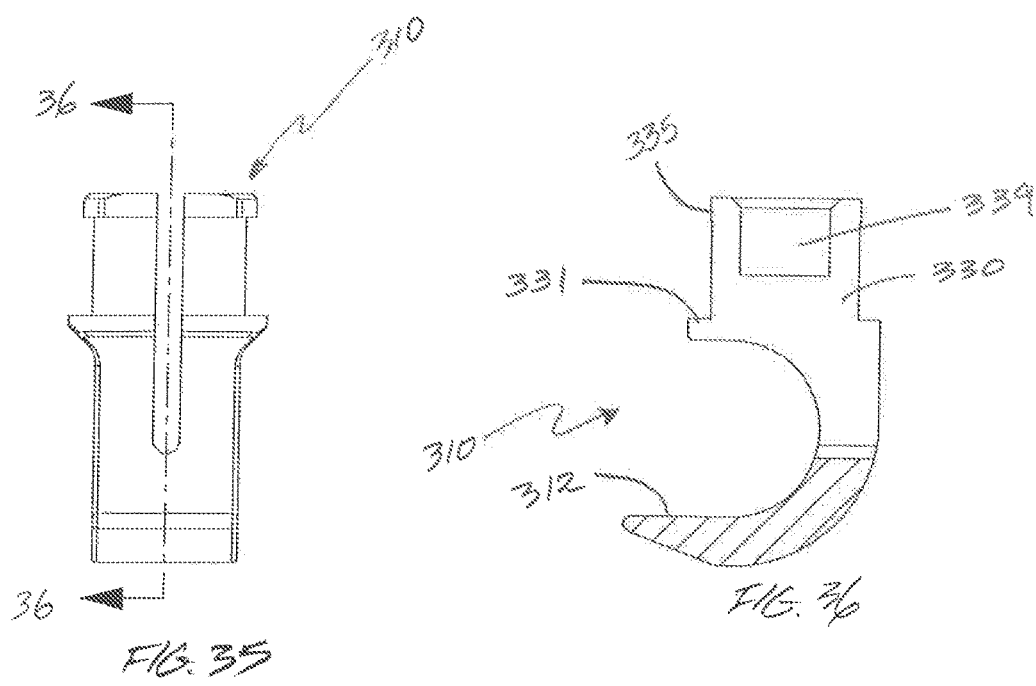
FIG. 35
FIG. 36
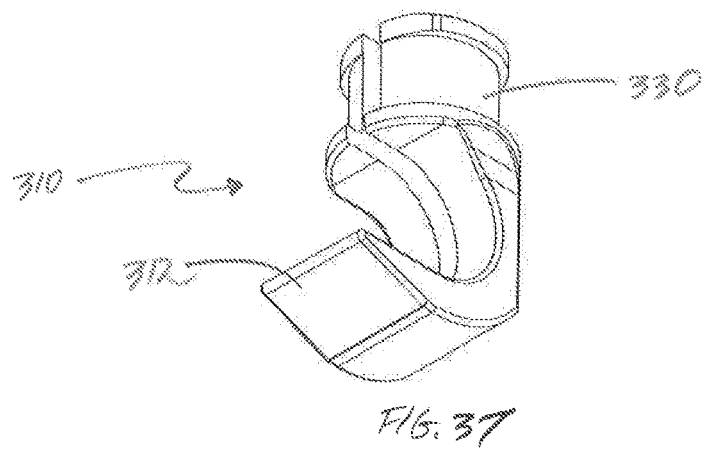
FIG. 37

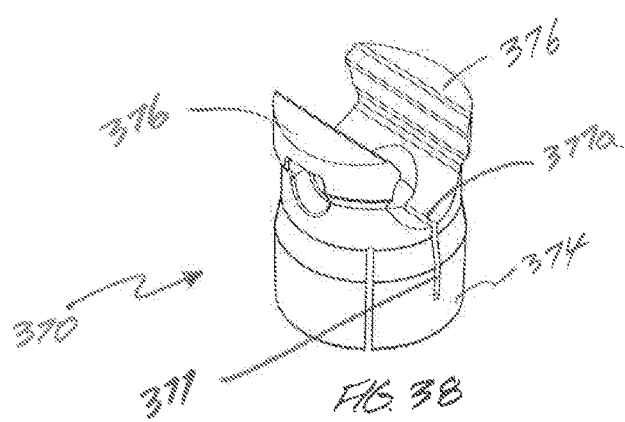
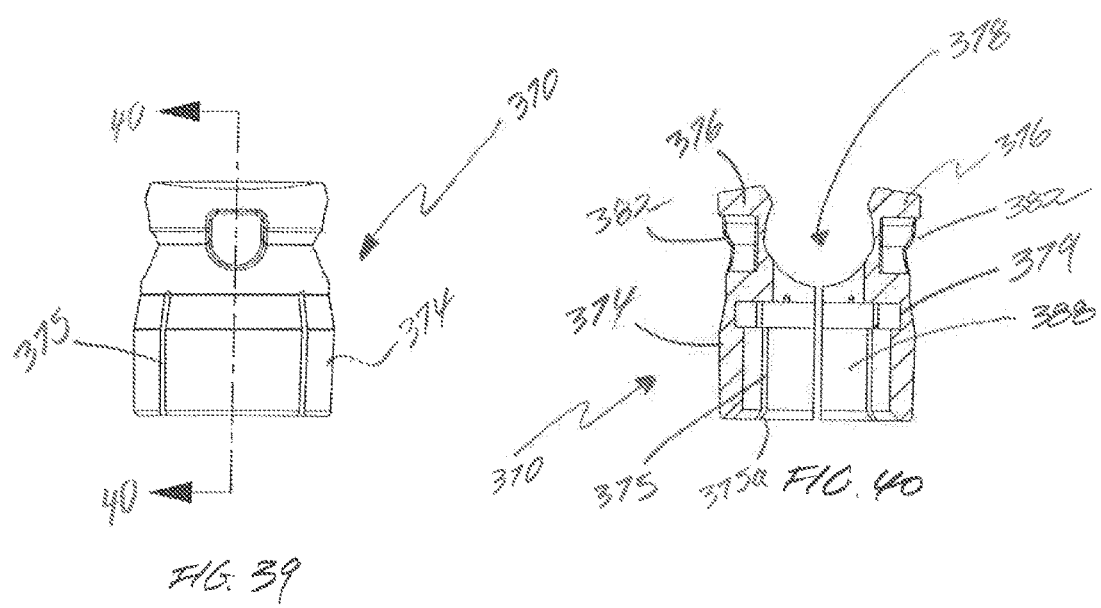
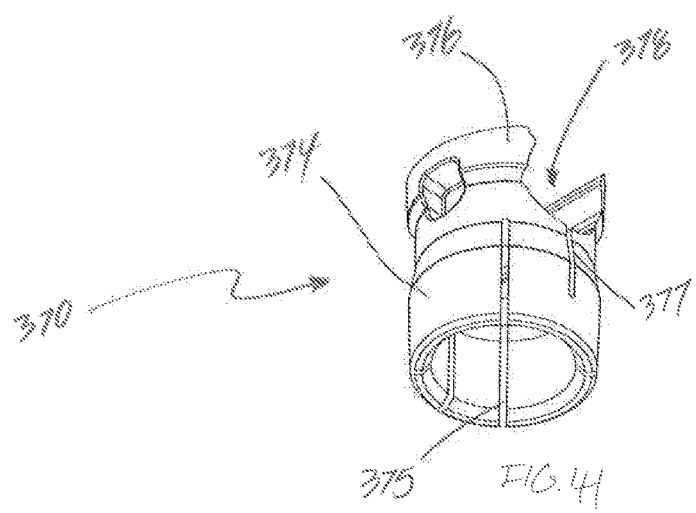

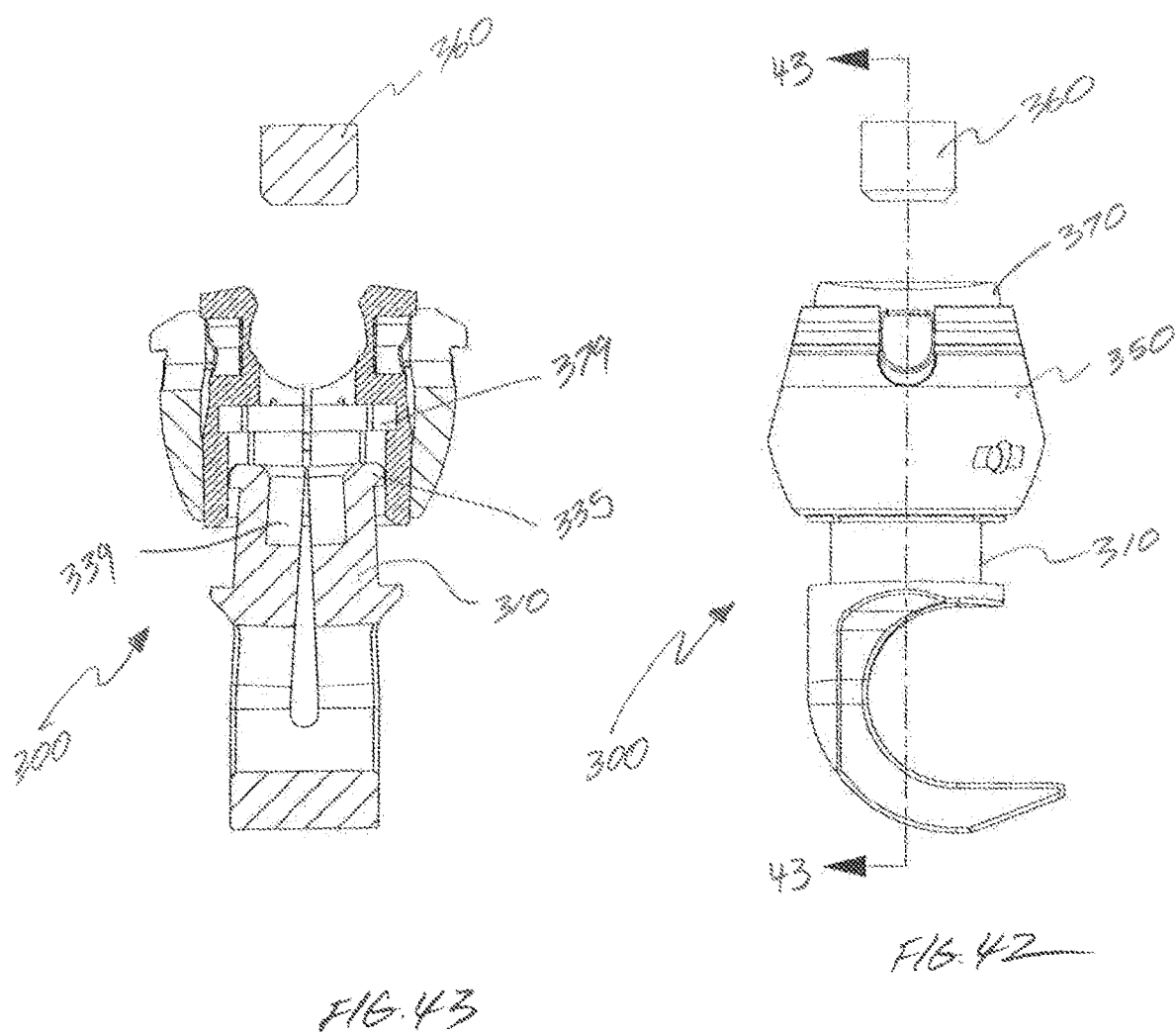

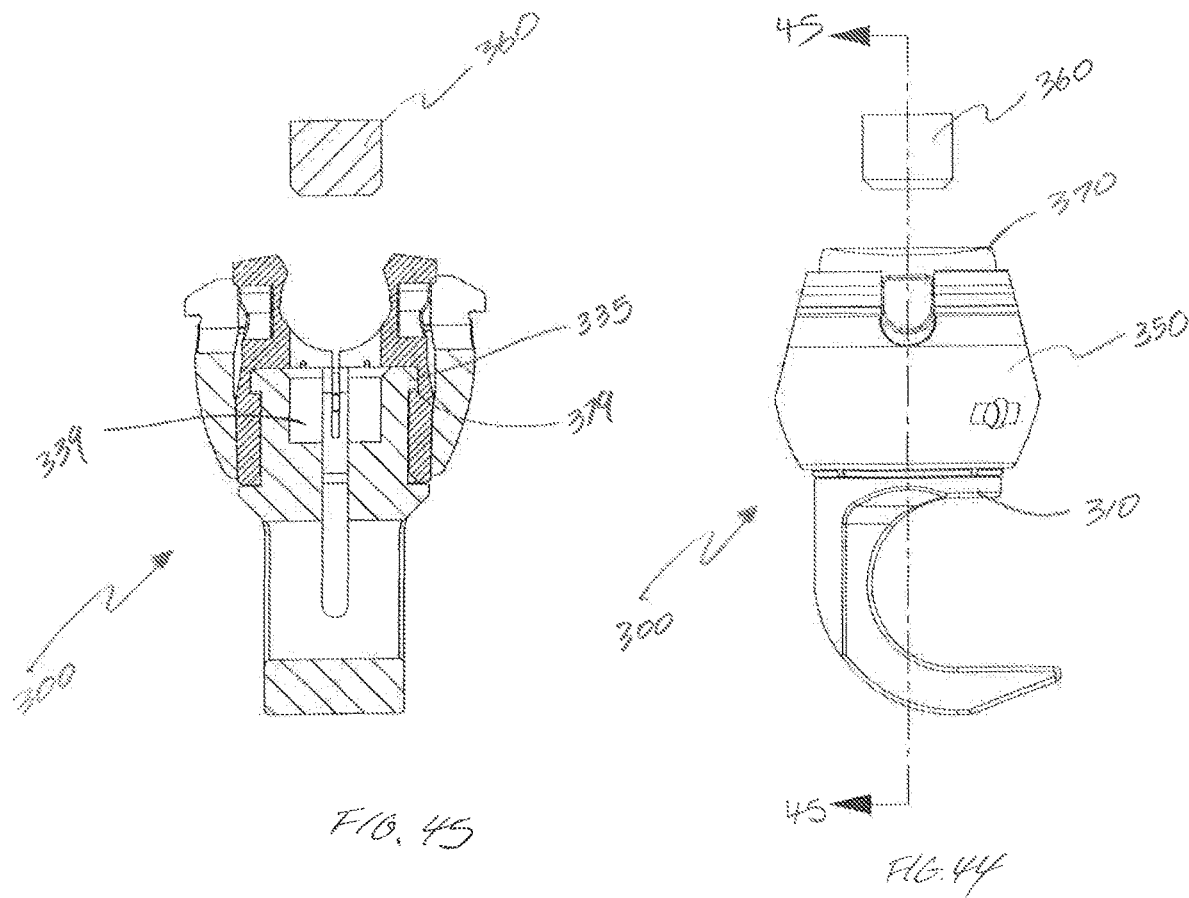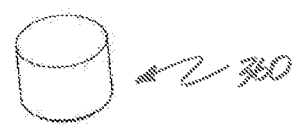

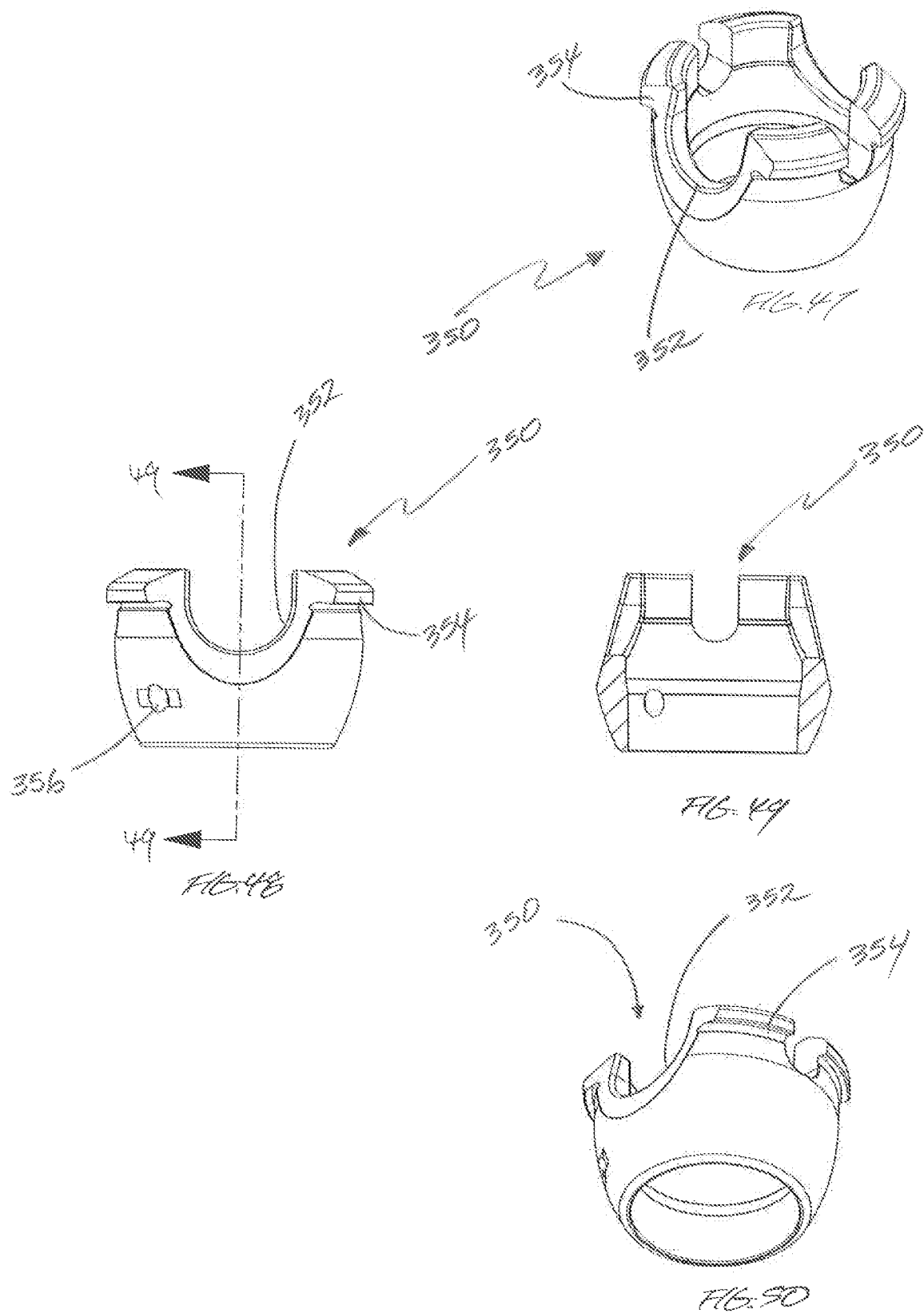

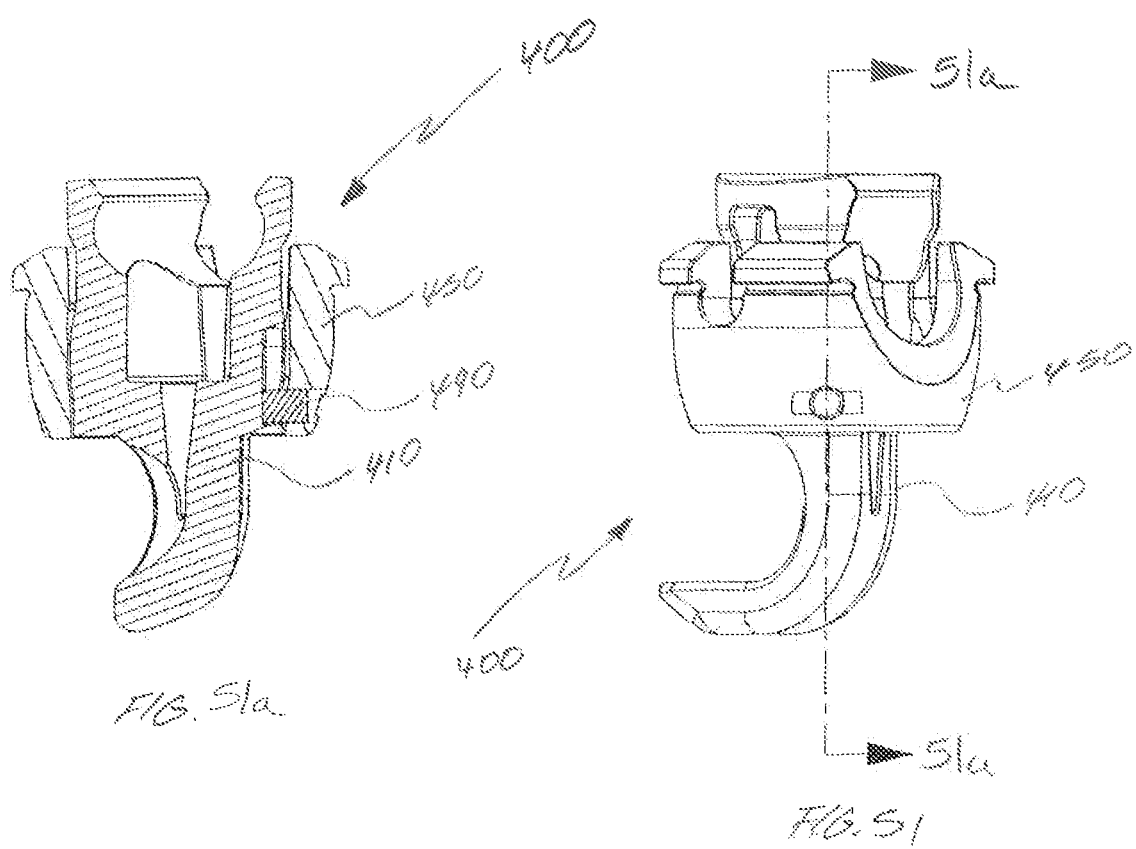

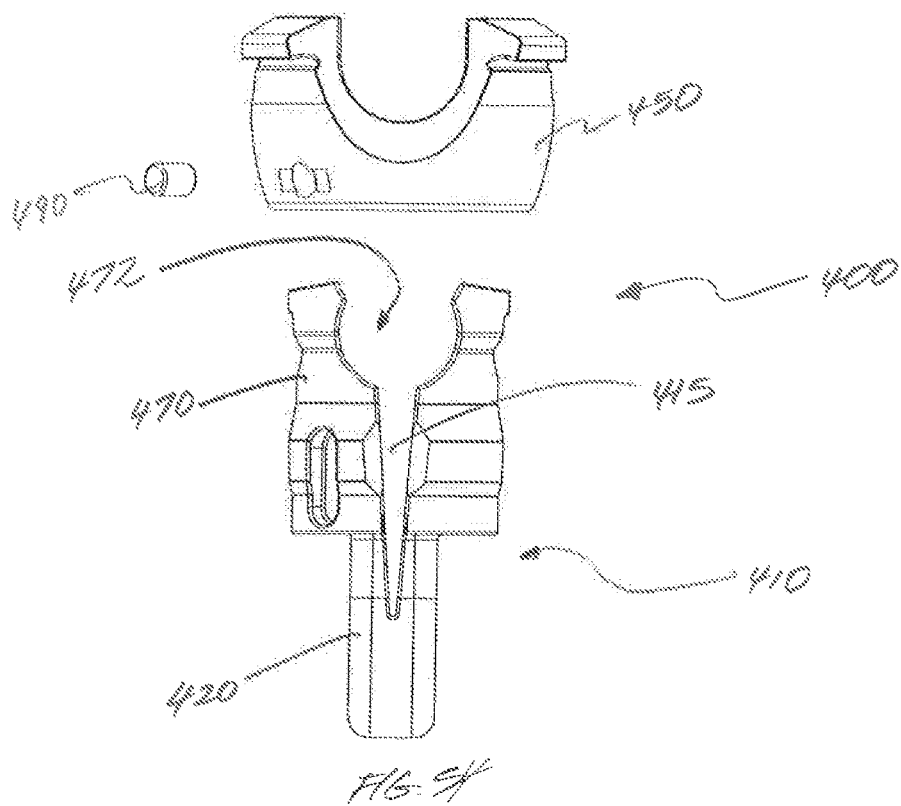
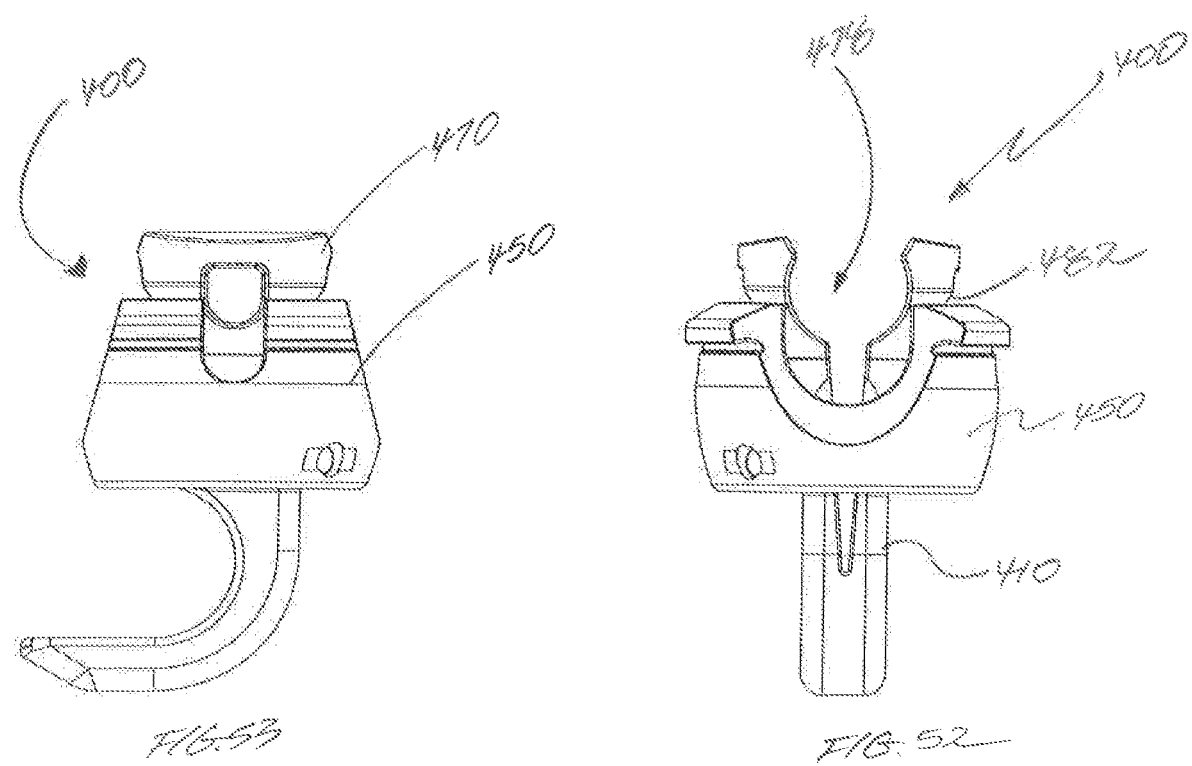

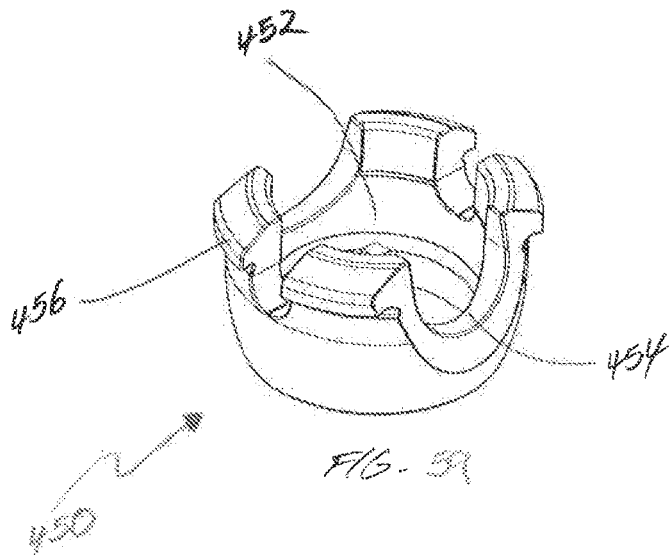
FIG. 59
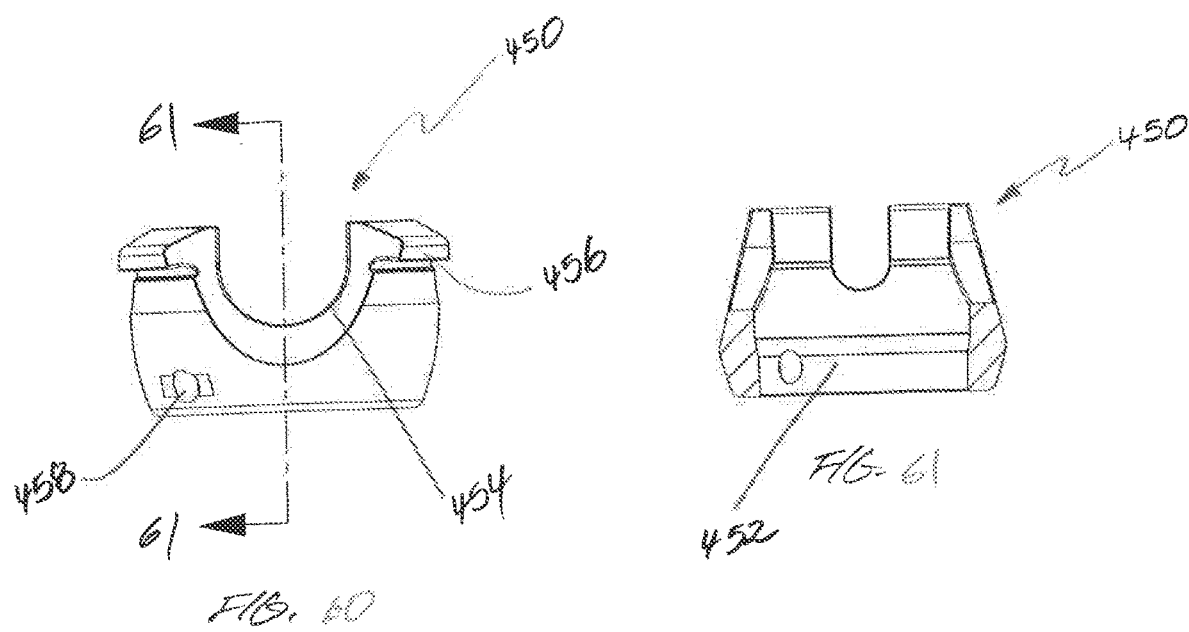
FIG. 60
FIG. 61
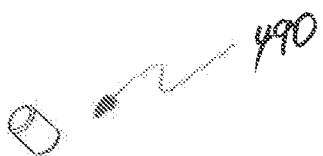
FIG. 62

TAPER LOCK HOOK

CROSS-REFERENCE TO RELATED APPLICATION

This application is a division of U.S. patent application Ser. No. 14/211,573, filed on Mar. 14, 2014, which claims priority to, and the benefit of, U.S. Provisional Patent Application Ser. No. 61/781,813, filed on Mar. 14, 2013, the entire contents of each of these prior applications are incorporated by reference herein.

BACKGROUND

Technical Field

The present disclosure relates to an orthopedic surgical device, and more particularly, to a taper lock hook.

Background of Related Art

Spinal implant systems have been developed to achieve immobilization of vertebral bodies of the spine in a particular spatial relationship to correct spinal irregularities and to restore stability to traumatized areas of the spine. These spinal implant systems may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina and entering into the central canal. In either case, the implants generally include elongate support rod elements which are coupled to the screws or hooks to immobilize several sequential vertebrae, for example to hold them stable so that adjacent bones may be fused with bone graft.

Such hook and rod assemblies generally include a plurality of hooks having rounded blade portions, flat extending members of which are inserted posteriorly under the lamina between the transverse process and the spinous process. The hooks further include upper body portions to which the support rod may be coupled. The rod extends along the axis of the spine, coupling to each of a plurality of hooks via receiving portions of their bodies. The aligning influence of the rod forces the spine to which it is affixed, to conform to a more proper shape.

It has been identified, however, that a considerable difficulty may be associated with inserting hooks under sequential lamina along a misaligned curvature and simultaneously precisely aligning their rod receiving portions with the rod to receive the rod therethrough without distorting, tilting, rotating, or exerting undesired translational forces on the hooks. Accordingly, there is a need for a hook that facilitates the process of inserting hooks under sequential lamina.

SUMMARY

In accordance with an embodiment of the present disclosure, there is provided a spinal hook including a hook member, an inner collet, and an outer portion. The hook member includes a head portion and a blade portion. The inner collet includes a base portion configured to rotatably engage the head portion and a pair of engaging portions defining a slot configured to receive a connecting rod therein. The outer portion is movable relative to the inner collet between a locked position in which the outer portion causes the pair of engaging portions to move toward each other and an unlocked position in which the outer portion causes the pair of engaging portions to be spread apart to facilitate insertion or removal of the connecting rod.

In an embodiment, the spinal hook may further include a retaining ring that is radially deflectable. The retaining ring may rotatably couple the head portion with the base portion, while inhibiting axial movement therebetween.

In another embodiment, the head portion may define a circumferential groove configured to receive at least a portion of the retaining ring therein. The base portion of the inner collet may include an annular groove configured to receive a portion of the retaining ring disposed in the circumferential groove of the head portion. Each of the pair of engaging portions may include a surface configured to engage an inner surface of the outer portion to transition the outer portion between the locked and unlocked positions. In particular, the surface may be tapered such that in the unlocked position, the surface may be spaced apart from the inner surface of the outer portion.

In yet another embodiment, the outer portion may include a pin and the inner collet may define a slot configured to slidably engage the pin therein. In addition, the inner collet may include a plurality of longitudinal slits configured to enable radial deflection of the inner collet.

In accordance with yet another embodiment of the present disclosure, there is provided a spinal hook including a hook housing member and an inner collet slidably associated with the hook housing member. The hook housing member includes a head portion and a blade portion. The inner collet includes a pair of engaging portions defining a first slot therebetween. The first slot is configured to receive a connecting rod therein. The inner collet is transitionable between an unlocked state in which the pair of engaging portions are spaced apart to receive the connecting rod within the first slot and a locked state in which the pair of engaging portions secure the connecting rod within the first slot.

In an embodiment, the inner collet may include a second slot and the head portion of the hook housing member may include a pin configured to slidably engage the second slot of the inner collet. The inner collet may include a slit extending along a length thereof to facilitate radial deflection of the inner collet.

In another embodiment, the spinal hook may further include a retaining member configured to be disposed in a recess defined in the inner collet, whereby the retaining member causes the inner collet to expand radially outward such that a portion of the inner collet is selectively positionable within the head of the hook housing member.

In yet another embodiment, the head portion and the blade portion of the hook housing member may be monolithically formed. At least a portion of the inner collet may be slidably disposed within the head portion of the hook housing member. The slit may have an opening leading into the first slot.

In still another embodiment, each of the pair of engaging portions may include a surface configured to engage an inner surface of the head portion to transition the inner collet between the locked and unlocked states. In particular, the surface may be tapered such that in the unlocked state, the surface is spaced apart from the inner surface of the head portion.

BRIEF DESCRIPTION OF THE DRAWINGS

Various embodiments of the present disclosure are described hereinbelow with reference to the drawings, wherein:

FIG. 4 is an exploded side view of the spinal hook of FIG. 1 with parts separated;

FIG. 5 is a cross-sectional view of the spinal hook of FIG. 1 cut along a section line "5-5" in FIG. 1;

FIG. 6 is a perspective view of a hook member of the spinal hook of FIG. 1;

FIG. 7 is a side cross-sectional view of the hook member of FIG. 6;

FIG. 8 is a perspective view of an inner collet of the spinal hook of FIG. 1;

FIG. 9 is a side view of the inner collet of FIG. 8;

FIG. 10 is a cross-sectional view of the inner collet of FIG. 9 cut along a section line "10-10" in FIG. 9;

FIG. 11 is a bottom perspective view of the inner collet of FIG. 10 illustrating a recess therein;

FIG. 12 is a perspective view of a taper lock head of the spinal hook of FIG. 1;

FIG. 13 is a top view of the taper lock head of FIG. 12;

FIG. 14 is a side view of the taper lock head of FIG. 12;

FIG. 15 is a cross-sectional view of the taper lock head of FIG. 14 cut along a section line "15-15" in FIG. 14;

FIG. 16 is a bottom perspective view of the taper lock head of FIG. 14;

FIG. 17 is a perspective view of a retaining ring of the spinal hook of FIG. 1;

FIG. 21 is a top view of the spinal hook of FIG. 18;

FIG. 22 is an exploded side view of the spinal hook of FIG. 18;

FIG. 23 is a perspective view of a hook housing member of the spinal hook of FIG. 18;

FIG. 24 is a bottom perspective view of the hook housing member of FIG. 23;

FIG. 25 is a side cross-sectional view of the hook housing member of FIG. 24;

FIGS. 30-30b are perspective views of the spinal hook of FIG. 18 illustrating use with a connecting rod.

FIG. 31a is a cross-sectional view of the spinal hook of FIG. 31 cut along a section line "31a-31a" in FIG. 31.

FIG. 31b is a rear view of the spinal hook of FIG. 31;

FIG. 34 is a perspective view of a hook member of the spinal hook of FIG. 31;

FIG. 35 is a rear view of the hook member of FIG. 34;

FIG. 36 is a cross-sectional view of the hook member of FIG. 35 cut along a section line "36-36" in FIG. 35;

FIG. 37 is a bottom perspective view of the hook member of FIG. 35;

FIG. 38 is a perspective view of an inner collet of spinal hook of FIG. 35;

FIG. 39 is a side view of the inner collet of FIG. 38;

FIG. 40 is a cross-sectional view of the inner collet of FIG. 39 cut along a section line "40-40" in FIG. 39;

FIG. 41 is a bottom perspective view of the inner collet of FIG. 39;

FIG. 42 is a perspective view of the spinal hook of FIG. 31 with a retaining member removed therefrom, illustrating a lip of a hook member disengaged from an annular groove of an inner collet;

FIG. 43 is a cross-sectional view of the spinal hook of FIG. 42 cut along a section line "43-43" in FIG. 42;

FIG. 44 is a side view of the spinal hook of FIG. 31 with a retaining member removed therefrom, illustrating the lip of a hook member engaged with the annular groove of the inner collet;

FIG. 45 is a cross-sectional view of the spinal hook of FIG. 44 cut along a section line "45-45" in FIG. 44;

FIG. 46 is a perspective view of a retaining member of the spinal hook of FIG. 31;

FIG. 47 is a perspective view of a taper lock head of the spinal hook of FIG. 31;

FIG. 48 is a side view of the taper lock head of FIG. 47;

FIG. 49 is a cross-sectional view of the taper lock head of FIG. 48 cut along a section line "49-49" in FIG. 48;

FIG. 50 is a bottom perspective view of the taper lock head of FIG. 48;

FIG. 51 is a perspective view of a spinal hook in accordance with yet another embodiment of the present disclosure;

FIG. 51a is a cross-sectional view of the spinal hook of FIG. 51 cut along a section line "51a-51a" in FIG. 51;

FIG. 52 is a rear view of the spinal hook of FIG. 51;

FIG. 53 is a side view of the spinal hook of FIG. 51;

FIG. 54 is an exploded rear view of the spinal hook of FIG. 51 with parts separated;

FIG. 59 is a perspective view of a taper lock head of the spinal hook of FIG. 51;

FIG. 60 is a side view of the taper lock head of FIG. 59;

FIG. 61 is a cross-sectional view of the taper lock head of FIG. 60 cut along a section line "61-61" in FIG. 60; and FIG. 62 is a perspective view of a pin of the spinal hook of FIG. 51.

DETAILED DESCRIPTION OF EMBODIMENTS

Figure 1:
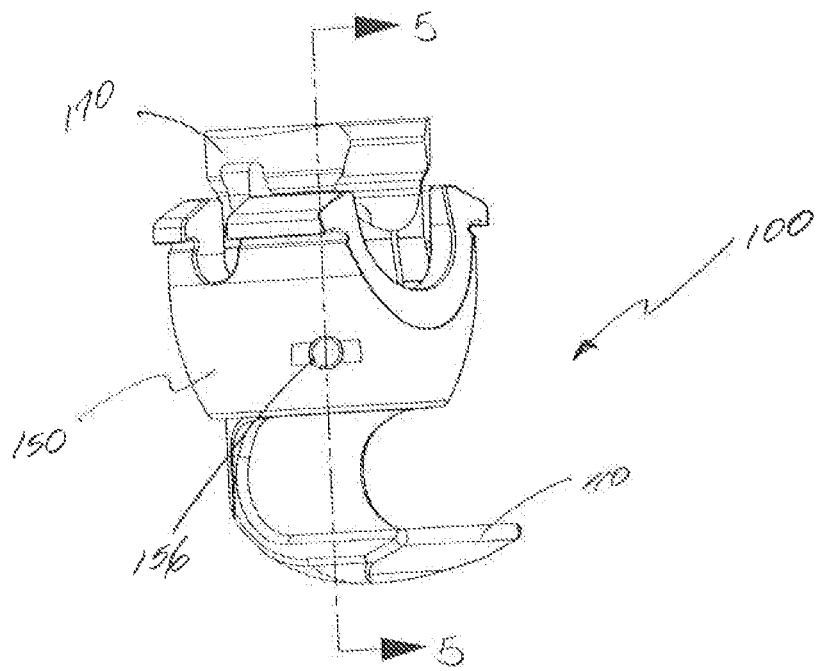
FIG. 1 is a perspective view of a spinal hook in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal,"

will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-4, an embodiment of the present disclosure is shown generally as a spinal hook 100. Spinal hook 100 is configured to provide coupling of a connecting rod 1000 (FIG. 30) to the spine by being anchored on, e.g., the undersurface of the lamina which forms a shallow arch or an inverted—V shape. Spinal hook 100 includes a hook member 110, a taper lock head 150, and an inner collet 170. Taper lock head 150 is configured to slide over at least a portion of inner collet 170 to releasably secure connecting rod 1000 within a slot 178 (FIG. 2) defined in inner collet 170, as will be discussed hereinbelow.

With reference now to FIGS. 5-7, hook member 110 includes a blade portion 112 and a head portion 130. Head portion 130 is generally cylindrical and defines a circumferential groove 132 configured to receive a retaining ring 160 (FIG. 4). Head portion 130 is configured to rotatably engage inner collet 170.

With reference to FIGS. 8-11, inner collet 170 includes a base portion 174 and a pair of engaging members 176 extending from base portion 174. Engaging members 176 define a generally U-shaped slot 178 configured to receive connecting rod 1000 therein. Each engaging member 176 includes a surface 182 configured to engage an inner surface of taper lock head 150 to secure connecting rod 1000 in slot 178, as will be discussed hereinbelow. Surface 182 is tapered, whereby when taper lock head 150 is in the unlocked position, an inner surface of taper lock head 150 is disengaged from surface 182. Base portion 174 is generally cylindrical and defines a recess 188 having a complementary configuration to head portion 130 of hook member 110. Under such a configuration, at least a portion of head portion 130 is rotatably received within recess 188. Base portion 174 defines a plurality of slits 175 configured to enable radial deflection of base portion 174. In addition, inner collet 170 further defines slits 177 extending from base portion 174 to slot 178, such that slit 177 leads into slot 178. Slits 175, 177 have respective openings 175a, 177a (FIG. 10). Openings 175a, 177a may be disposed on opposing ends of base portion 174 to enable radial deflection in both ends of base portion 174. Recess 188 of base portion 174 defines an annular groove 179 (FIG. 10) configured to engage at least a portion of retaining ring 160. In particular, retaining ring 160 is positioned in circumferential groove 132 defined in head portion 130 of hook member 110. A portion of retaining ring 160 extends radially outward from circumferential groove 132 and is received in annular groove 179 of inner collet 170. Under such a configuration, hook member 110 and inner collet 170 are rotatable relative to each other, while hook member 110 and inner collet 170 are secured to each other to inhibit relative axial movement therebetween. Annular groove 179 of inner collet 170 and circumferential groove 132 of hook member 110 are dimensioned to enable radial deflection of retaining ring 160, while rotatably securing inner collet 170 with hook member 110. With particular reference to FIGS. 8 and 9, base portion 174 includes a slot 180 configured to slidably engage a pin 190 (FIG. 4) coupled with taper lock head 150, as will be discussed hereinbelow.

With reference now to FIGS. 11-16, taper lock head 150 is configured to slidably engage inner collet 170 to releasably secure connecting rod 1000 within slot 178 defined by engaging members 176 of inner collet 170. In particular, taper lock head 150 defines a pair of diametrically opposing cut out portions 152 to accommodate connecting rod 1000 therein. In addition, taper lock head 150 includes lips 154 extending radially outward. Lips 154 are configured to engage a surgical instrument (not shown) to slide taper lock head 150 against inner collet 170 to lock/unlock connecting rod 1000.

Figure 2:
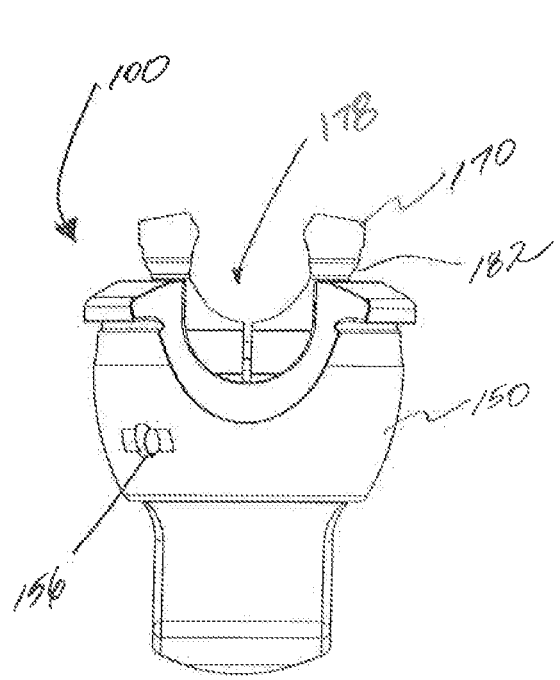
FIG. 2 is a rear view of the spinal hook of FIG. 1.
Figure 3:
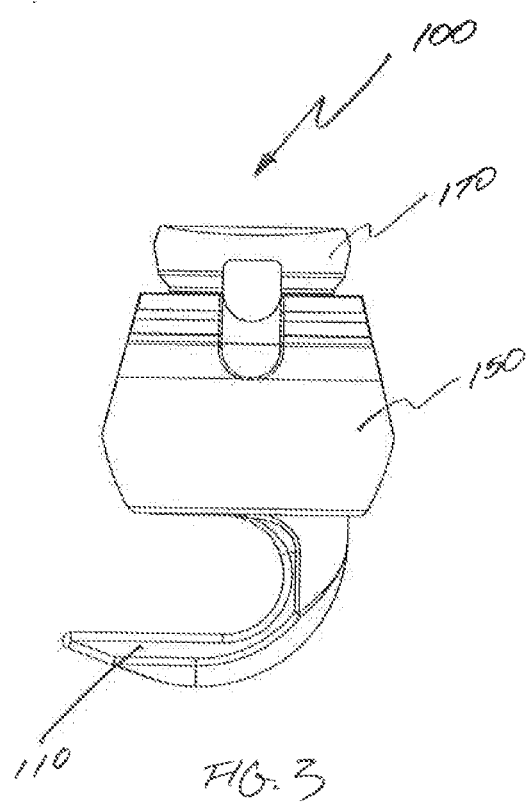
FIG. 3 is a side view of the spinal hook of FIG. 1.

With brief reference back to FIGS. 1 and 2, taper lock head 150 includes a bore 156 configured to secure pin 190 therein. Pin 190 is coupled with taper lock head 150. Pin 190 slides against slot 180 (FIG. 8) of inner collet 170 to facilitate and secure sliding movement of taper lock head 150 against inner collet 170. Furthermore, pin 190 (FIG. 5) is configured to maintain rotational alignment between inner collet 170 and taper lock head 150.

With brief reference back to FIG. 5, taper lock head 150 is transitionable between an unlocked position and a locked position. In the unlocked position, the pair of engaging members 176 of inner collet 170 is spread apart. In particular, an inner surface of taper lock head 150 is disengaged (spaced apart) from the tapered surface 182. In this manner, engaging members 176 of inner collet 170 are spaced wider than a diameter of connecting rod 1000 to facilitate insertion of connecting rod 1000 into slot 178 or to facilitate removal of connecting rod 1000 from slot 178. To transition taper lock head 150 from the unlocked position to the locked position, taper lock head 150 is slidably moved away from hook member 110 over inner collet 170. In the locked position, the inner surface of taper lock head 150 engages surface 182 of engaging member 176, which, in turn, causes engaging members 176 to move toward each other. In this manner, connecting rod 1000 disposed within slot 178 is secured within slot 178.

In use, spinal hook 100 is positioned on a desired spinal portion, such that blade portion 112 engages the desired spinal portion. Connecting rod 1000 is then placed in slot 178 of inner collet 170. At this time, taper lock head 150 may be slightly moved away from blade portion 112 to partially lock connecting rod 1000 within slot 178. Partially locking connecting rod 1000 enables spinal hook 100 to slide along connecting rod 1000. Inner collet 170 may be rotated about head portion 130 of hook member 110 to achieve desired relative orientation between hook member 110 and inner collet 170. Once the desired orientation is achieved, taper lock head 150 may be transitioned to the locked position to completely secure connecting rod 1000 within slot 178 of inner collet 170.

With reference now to FIGS. 18-22, another embodiment of the present disclosure is shown generally as a spinal hook 200. Spinal hook 200 includes a hook housing member 210, a retaining member 260, and an inner collet 270. In contrast to spinal hook 100, inner collet 270 of spinal hook 200 moves within hook housing member 210 to releasably secure connecting rod 1000 within a slot 278 defined in inner collet 270, as will be discussed hereinbelow.

With reference now to FIGS. 23-25, hook housing member 210 includes a blade portion 212 and a head portion 230. Blade portion 212 and head portion 230 are formed as a unitary construct and may be monolithically formed. Head portion 230 is generally cylindrical and defines an opening 232 configured to receive retaining member 260 and inner collet 270 therein. Head portion 230 of hook housing member 210 defines a pair of diametrically opposing cut out portions 252 to accommodate connecting rod 1000 therethrough. In addition, head portion 230 further includes lips 254 extending radially outward.

Figure 18A:
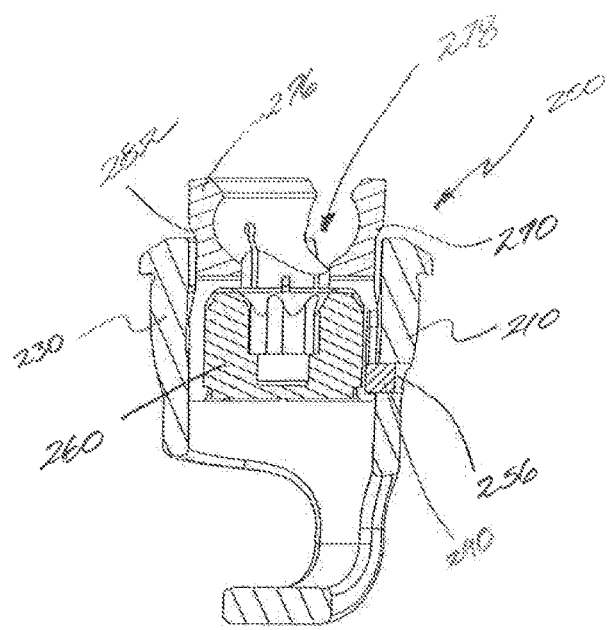
FIG. 18a is a cross-sectional view of the spinal hook of FIG. 18 cut along a section line "18a-18a" in FIG. 18.
Figure 18:
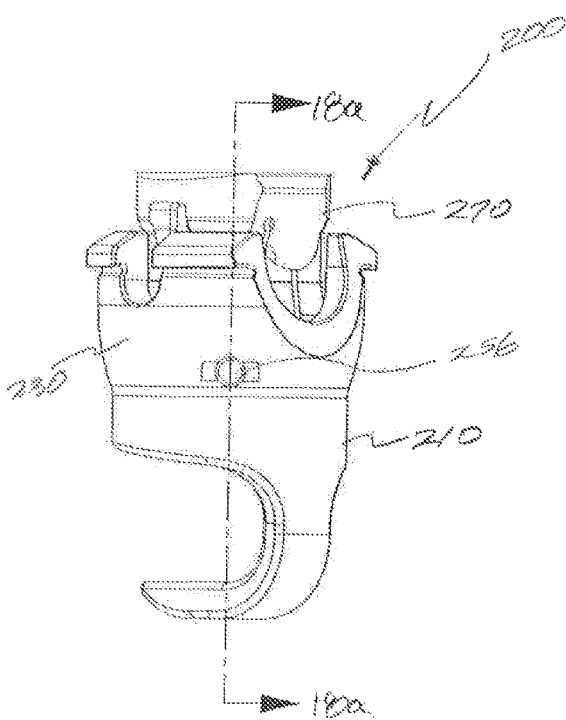
FIG. 18 is a perspective view of a spinal hook in accordance with another embodiment of the present disclosure.
Figure 19:
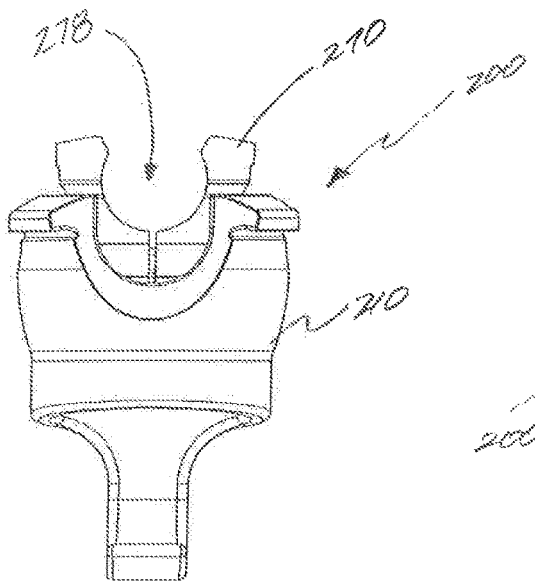
FIG. 19 is a rear view of the spinal hook of FIG. 18.
Figure 20:
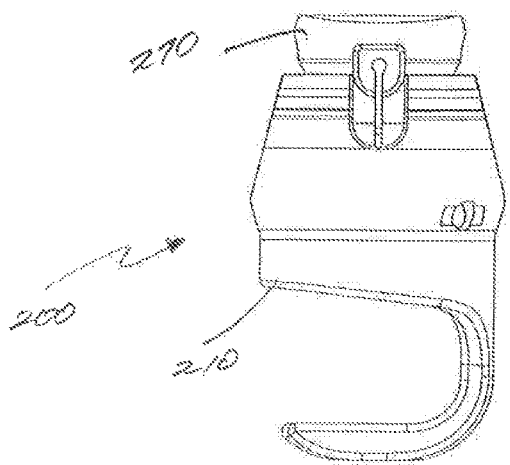
FIG. 20 is a side view of the spinal hook of FIG. 18.

With brief reference back to FIGS. 18 and 18a, head portion 230 of hook housing member 210 defines a bore 256 configured to secure pin 290 therein. Pin 290 is configured to slide within slot 280 (FIG. 27) of base portion 274 of inner collet 270 to facilitate sliding movement of inner collet 270 within opening 232 of hook housing member 210. Under such a configuration, rotational relationship between head portion 230 and inner collet 270 is maintained.

With reference now to FIGS. 22 and 27-29, inner collet 270 includes a base portion 274 and a pair of engaging members 276 extending from base portion 274. Engaging members 276 define a generally U-shaped slot 278 configured to receive connecting rod 1000 therein. Each engaging member 276 includes a surface 282 (FIGS. 18a and 29) configured to engage an inner surface of head portion 230 of hook housing member 210 to secure connecting rod 1000 in slot 278, as will be discussed hereinbelow. Surface 282 is tapered, such that when inner collet 270 is in the unlocked position, an inner surface of head portion 230 is disengaged/spaced apart from surface 282 (FIG. 18a).

Figure 26:
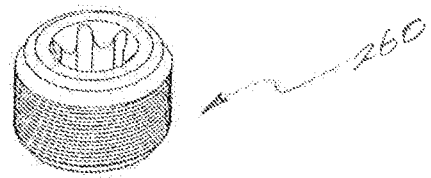
FIG. 26 is a perspective view of a retaining member of the spinal hook of FIG. 18.
Figure 27:
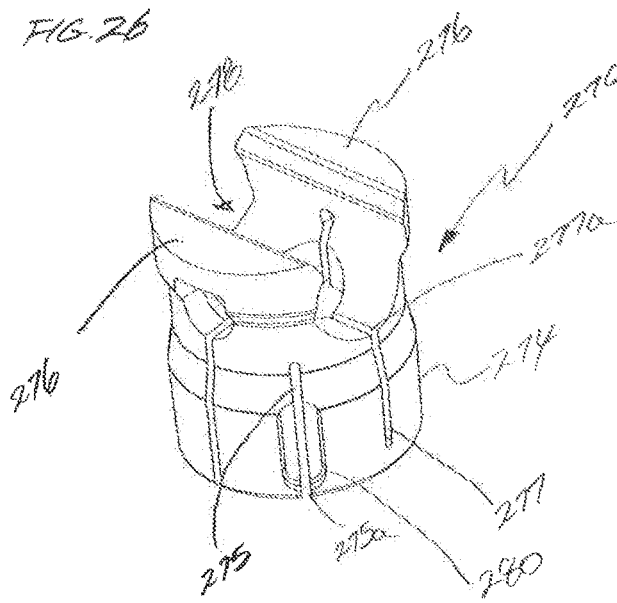
FIG. 27 is a perspective view of an inner collet of the spinal hook of FIG. 18.
Figure 28:
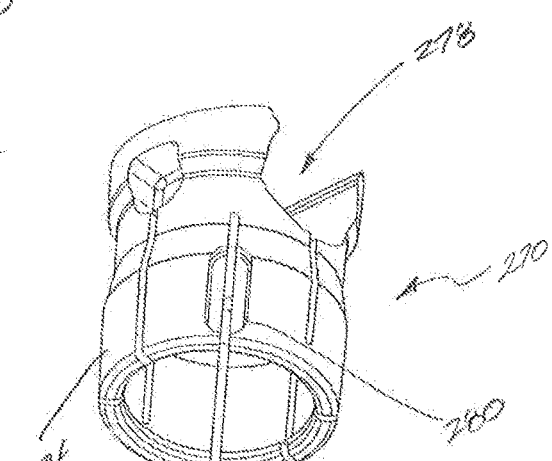
FIG. 28 is a bottom perspective view of the inner collet of FIG. 27.
Figure 29:
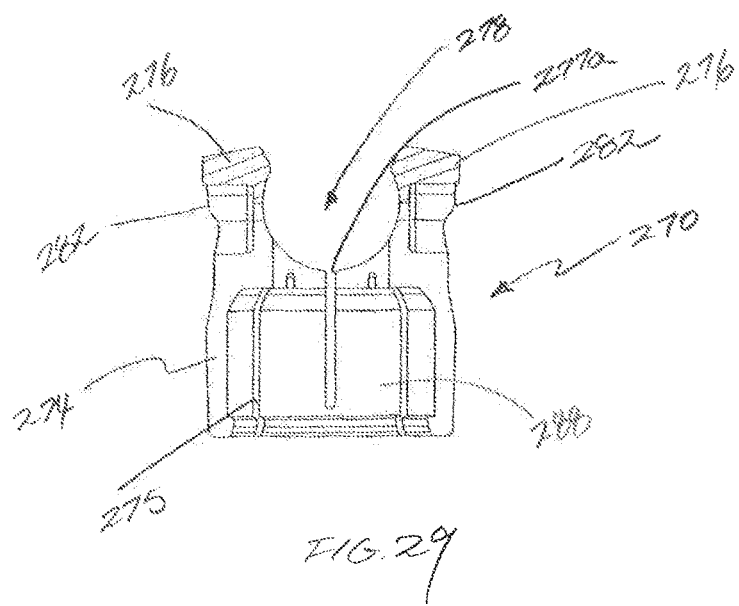
FIG. 29 is a side cross-sectional view of the inner collet of FIG. 27.

With particular reference to FIGS. 27-29, base portion 274 is generally cylindrical and defines a recess 288 (FIG. 29) having a complementary configuration to retaining portion 260 (FIG. 26). Base portion 274 defines a plurality of slits 275 configured to enable radial deflection of base portion 274. In addition, inner collet 270 further defines slits 277 extending from base portion 274 to slot 278, such that slit 277 opens into slot 278. Slits 275, 277 have respective openings 275a, 277a. Openings 275a, 277a may be disposed on opposing ends of base portion 274 to enable radial deflection in both ends of base portion 274. Base portion 274 is biased radially inward and engaging members 276 are biased radially outward. Slits 275, 277 of base portion 274 enable base portion 274 to deflect radially outward. Under such a configuration, retaining member 260 disposed within base portion 274 causes base portion 274 to extend radially outward to slidably secure inner collet 270 within opening 232 of hook housing member 210. Retaining member 260 applies a radially outward force against base portion 274 of inner collet 270, which, in turn, applies a radially outward force against an inner surface of hook housing member 210. In this manner, inner collet 270 is selectively positionable along a longitudinal axis "A-A" (FIG. 25).

With particular reference to FIGS. 27 and 28, base portion 274 of inner collet 270 includes a slot 280 configured to slidably engage a pin 290 (FIG. 22) coupled with hook housing member 210, as will be discussed hereinbelow.

Figure 30:
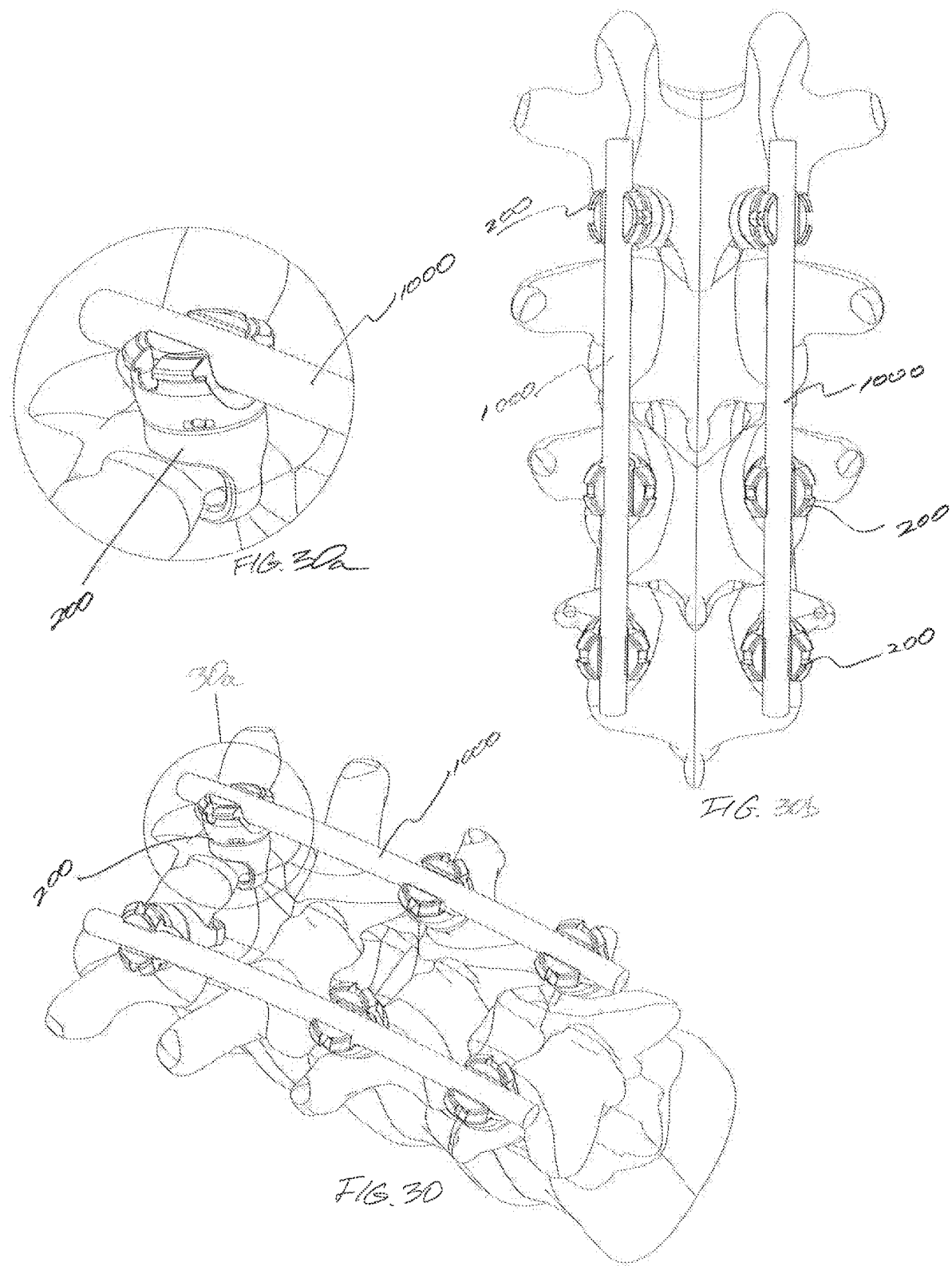
Figure 31:
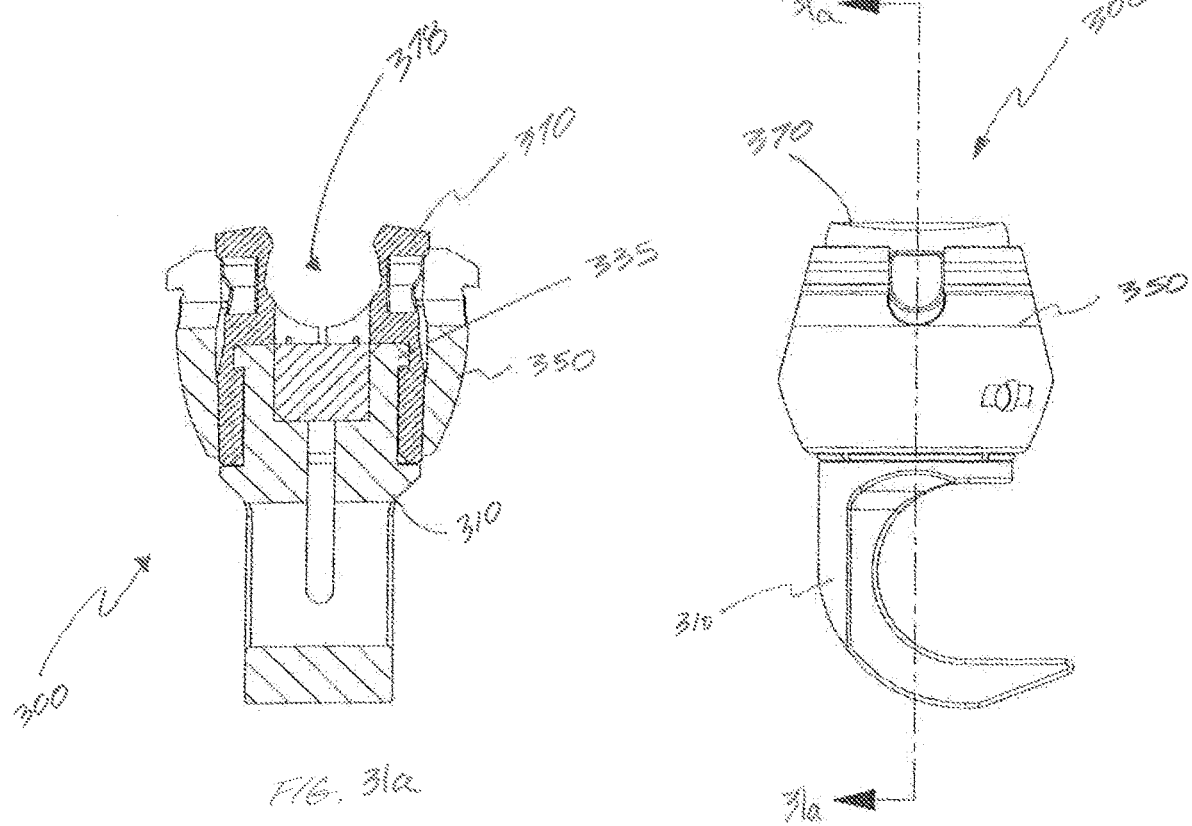
FIG. 31 is a perspective view of a spinal hook in accordance with yet another embodiment of the present disclosure.

With reference now to FIGS. 18a, 30, and 31, inner collet 270 is selectively movable along longitudinal axis "A-A" (FIG. 25) between a locked position and an unlocked position to releasably secure connecting rod 1000 within slot 278 defined by engaging members 276 of inner collet 270. In the unlocked position, the pair of engaging members 276 of inner collet 270 is spread apart. In particular, an inner surface of hook housing member 210 is disengaged from the tapered surface 282 (FIG. 18a). In this manner, engaging members 276 of inner collet 270 are spaced wider than a diameter of connecting rod 1000 to facilitate insertion of connecting rod 1000 into slot 278 or to facilitate removal of connecting rod 1000 from slot 278. To transition inner collet 270 from the unlocked position (FIG. 18a) to the locked position (FIG. 30), inner collet 270 is slidably moved toward blade portion 212 (FIG. 22) relative to head portion 230. In the locked position, the inner surface of hook housing member 210 engages surface 282 of engaging member 276, which, in turn, causes engaging members 276 to move toward each other. In this manner, connecting rod 1000 disposed within slot 278 is secured within slot 278.

In use, spinal hook 200 is positioned on a desired spinal portion, such that blade portion 212 engages the desired spinal portion. Connecting rod 1000 is then placed in slot 278 of inner collet 270. At this time, inner collet 270 may be transitioned to the locked position to completely secure connecting rod 1000 within slot 278 defined in inner collet 270.

Figure 32:
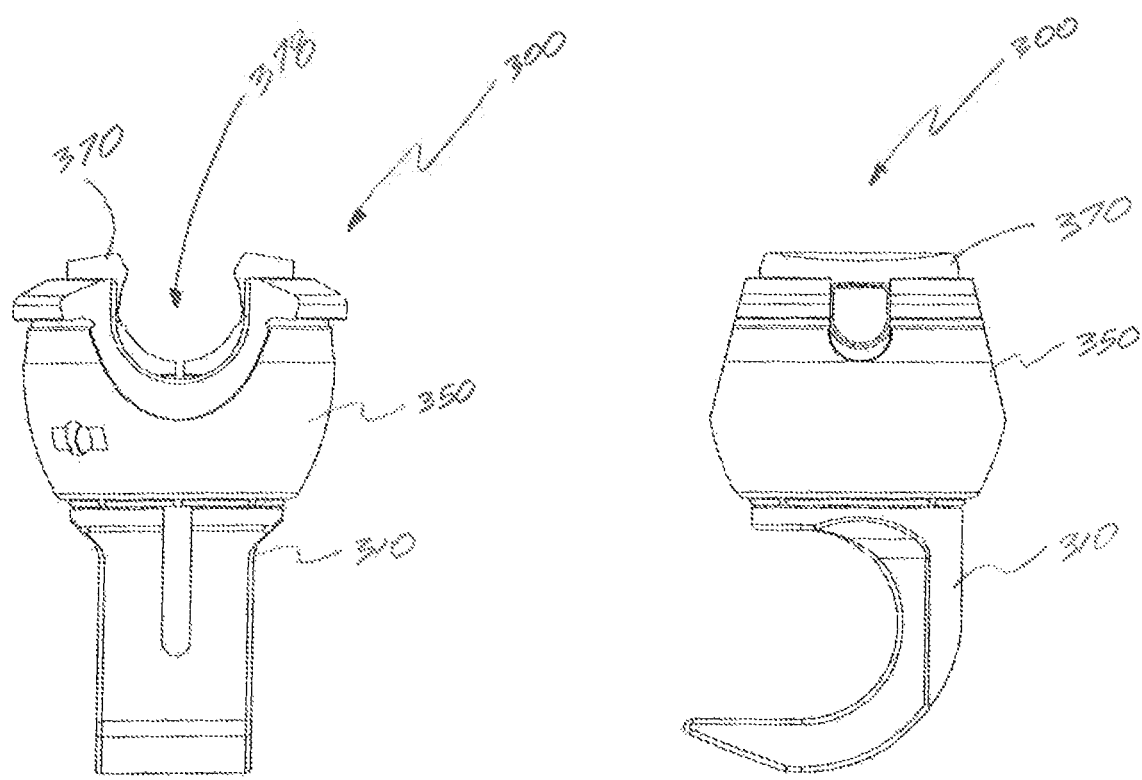
FIG. 32 is a side view of the spinal hook of FIG. 31.
Figure 33:
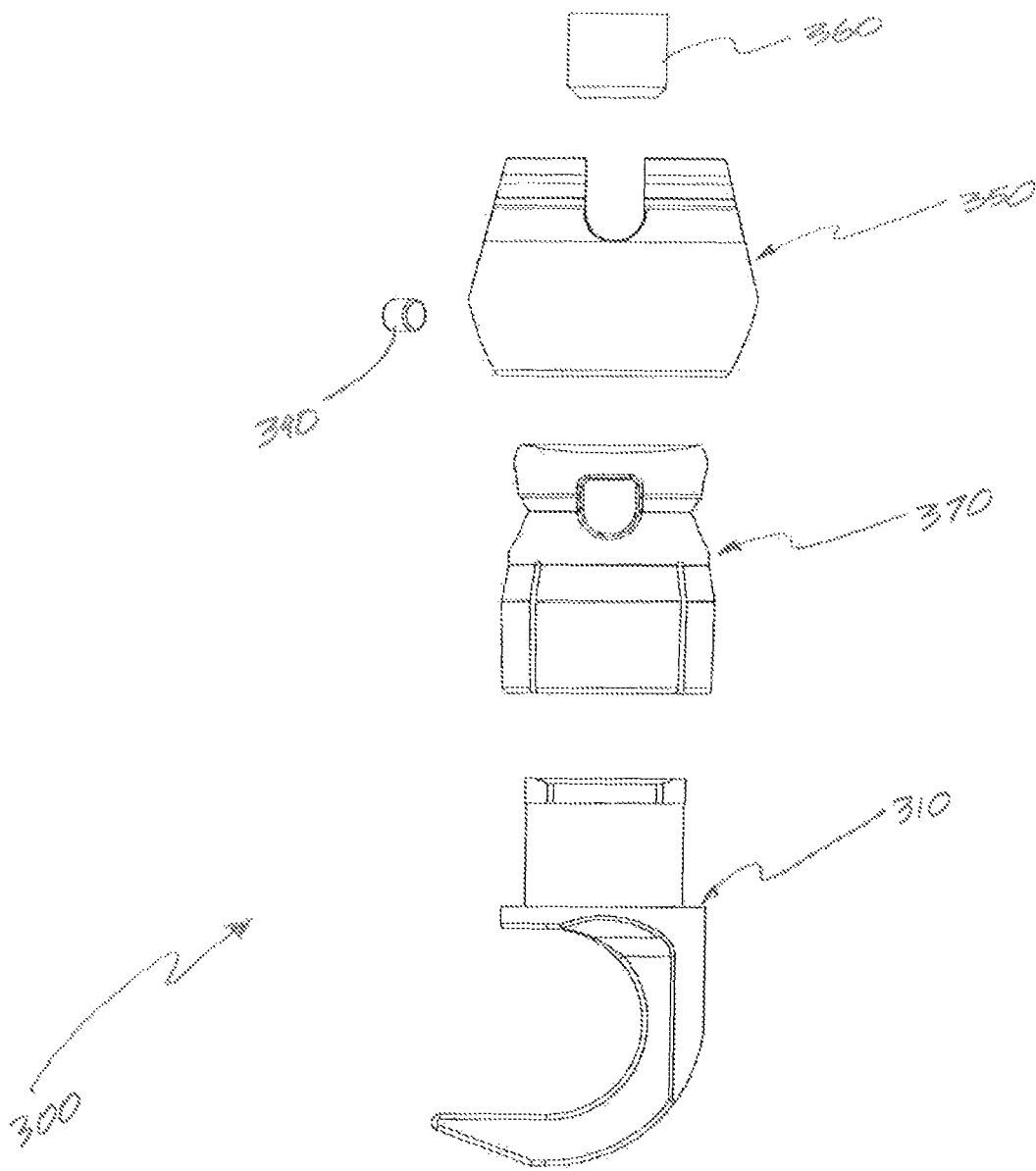
FIG. 33 is an exploded side view of the spinal hook of FIG. 31.
Figure 56:
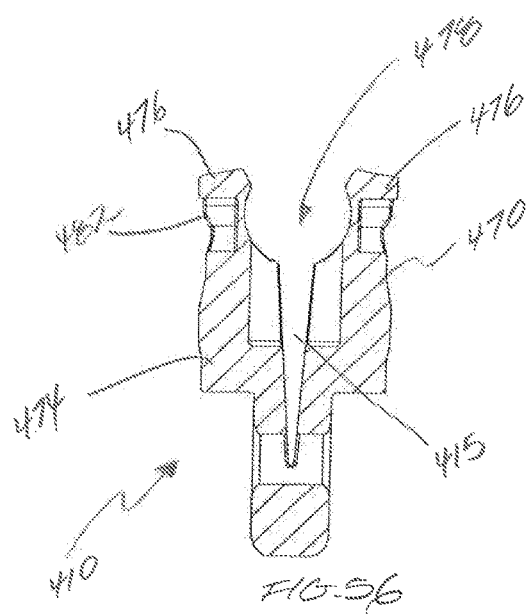
FIG. 56 is a cross-sectional view of the hook housing member of FIG. 55 cut along a section line "56-56" in FIG. 55.

With reference to FIGS. 31-33, still another embodiment of the present disclosure is shown generally as a spinal hook 300. Spinal hook 300 includes a hook member 310, a taper lock head 350, and an inner collet 370. Taper lock head 350 slides relative to hook member 310 to releasably secure connecting rod 1000 within a slot 378 defined in inner collet 370, as will be discussed hereinbelow.

With reference now to FIGS. 34-37, hook member 310 includes a blade portion 312 and a head portion 330. Head portion 330 is generally cylindrical and defines a pair of diametrically opposing slots 332 configured to enable radial deflection of head portion 330. Head portion 330 includes a base flange 331 configured to engage and support inner collet 370 and a lip 335 configured to engage an annular groove 379 defined in an inner surface of inner collet 370, as will be described below.

With reference to FIGS. 38-41, inner collet 370 includes a base portion 374 and a pair of engaging members 376 extending from base portion 374. Engaging members 376 define a generally U-shaped slot 378 configured to receive connecting rod 1000 therein. Each engaging member 376 includes a surface 382 (FIG. 40) configured to engage an inner surface of taper lock head 350 to secure connecting rod 1000 in slot 378. Surface 382 is tapered, such that when taper lock head 350 is in the unlocked position, an inner surface of taper lock head 350 is disengaged from surface 382. Base portion 374 is generally cylindrical and defines a recess 388 having a complementary configuration to head portion 330 of hook member 310. Under such a configuration, at least a portion of head portion 330 is rotatably received within recess 388. Base portion 374 defines a plurality of slits 375 configured to enable radial deflection of base portion 374. In addition, inner collet 370 further defines slits 377 extending from base portion 374 to slot 378, such that slit 377 leads into slot 378. Slits 375, 377 each have an opening 375a, 377a. Openings 375a, 377a may be disposed on opposing ends of base portion 374 to enable radial deflection in both ends of base portion 374. In addition, recess 388 of base portion 374 further defines an annular groove 379 (FIG. 40) configured to engage lip 335 of hook member 310. As discussed hereinabove, slots 332 defined in head portion 330 of hook member 310 enables radial deflection of head portion 330. Furthermore, head portion 330 is biased radially outward, whereby when head portion 330 is inserted into recess 388 of inner collet 370, lip 335 of hook member 310 engages annular groove 379 of inner collet 370, as best shown in FIGS. 43 and 45.

With particular reference to FIGS. 31a, 43, and 45, upon engaging lip 335 of hook member 310 within annular groove 379 of inner collet 370, retaining member 360 is inserted into cavity 339 defined in head portion 330 of hook member 310. Retaining member 360 causes head portion 330 to extend radially outward, thereby further securing hook member 310 to inner collet 370. Under such a configuration, hook member 310 and inner collet 370 are rotatable relative to each other, while hook member 310 and inner collet 370 are secured to each other to inhibit relative axial movement therebetween. Base portion 374 of inner collet 370 includes a slot (not shown) configured to slidably engage a pin 390 (FIG. 33) coupled with taper lock head 350, as will be discussed hereinbelow. In this manner, rotational relationship between inner collet 370 and taper lock head 350 is maintained.

With reference now to FIGS. 47-50, taper lock head 350 is configured to slidably engage inner collet 370 to releasably secure connecting rod 1000 within slot 378 defined by engaging members 376 of inner collet 370. In particular, taper lock head 350 defines a pair of diametrically opposing cut out portions 352 to accommodate connecting rod 1000 therethrough. In addition, taper lock head 350 includes lips 354 extending radially outward. Lips 354 are configured to engage a surgical instrument (not shown) to slide taper lock head 350 against inner collet 370 to lock/unlock connecting rod 1000.

With particular reference to FIG. 48, taper lock head 350 includes a bore 356 configured to secure pin 390 therein. Pin 390 is coupled with taper lock head 350 and slides against slot of inner collet 370 to facilitate and secure sliding movement of taper lock head 350 against inner collet 370.

Taper lock head 350 is transitionable between an unlocked position and a locked position. In the unlocked position, the pair of engaging members 376 of inner collet 370 is spread apart. In particular, an inner surface of taper lock head 350 is disengaged from the tapered surface 382. In this manner, engaging members 376 of inner collet 370 is spaced substantially wider than a diameter of connecting rod 1000 to facilitate insertion of connecting rod 1000 into slot 378 or to facilitate removal of connecting rod 1000 from slot 378. To transition taper lock head 350 to the locked position, taper lock head 350 is slidably moved away from hook member 310 relative to inner collet 370. In the locked position, the inner surface of taper lock head 350 engages surface 382 of engaging member 376, which, in turn, causes engaging members 376 to move toward each other. In this manner, connecting rod 1000 disposed within slot 378 is secured within slot 378.

In use, spinal hook 300 is positioned on a desired spinal portion, such that blade portion 312 engages the desired spinal portion. Connecting rod 300 is then placed in slot 378 of inner collet 370. At this time, taper lock head 350 may be slightly moved away from blade portion 312 to partially lock connecting rod 1000 within slot 378. Inner collet 370 may be rotated about head portion 330 of hook member 310 to achieve desired orientation of hook member 310 with respect to inner collet 370. Once the desired orientation is achieved, taper lock head 350 may be transitioned to the locked position to completely secure connecting rod 1000 within slot 378 defined in inner collet 370.

With reference to FIGS. 51-54, still yet another embodiment of the present disclosure is shown generally as a spinal hook 400. Spinal hook 400 includes a hook housing member 410 and a taper lock head 450. In contrast to spinal hook 100, inner collet portion 470 of spinal hook 400 is formed as a unitary construct with hook member 420 to releasably secure connecting rod 1000 within a slot 478 (FIG. 54) defined in inner collet portion 470, as will be discussed hereinbelow.

Figure 55:
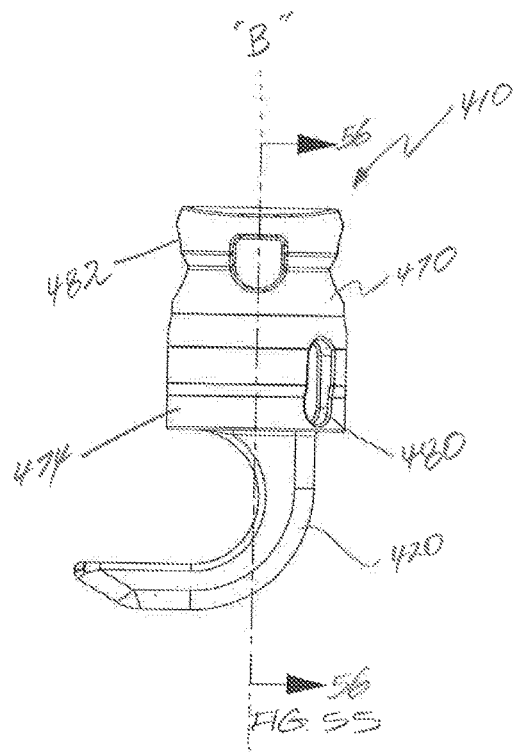
FIG. 55 is a side view of a hook housing member of the spinal hook of FIG. 51.
Figure 57:
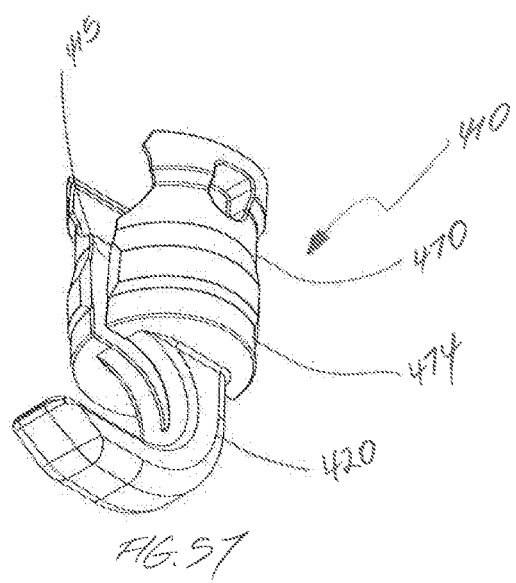
FIG. 57 is a front perspective view of the hook housing member of FIG. 55.
Figure 58:
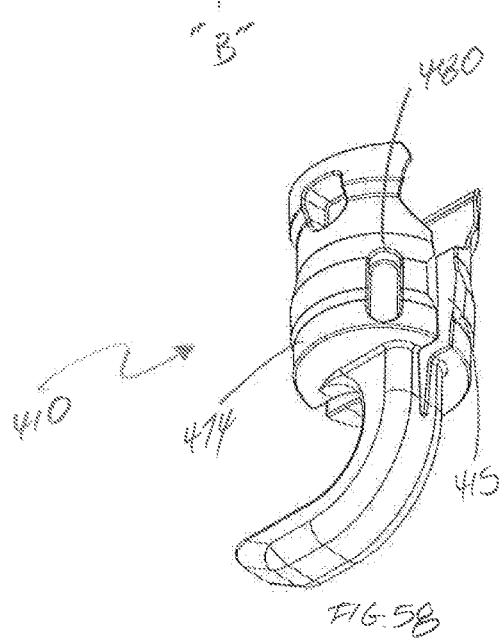
FIG. 58 is a bottom perspective view of the hook housing member of FIG. 55.

With reference now to FIGS. 55-58, hook housing member 410 includes a hook member 420 and an inner collet portion 470. Hook housing member 410 defines a longitudinal axis "B-B" (FIG. 55). Hook portion 420 and inner collet portion 470 are formed as a unitary construct and may be monolithically formed. Inner collet portion 470 includes a base portion 474 and a pair of engaging members 476 extending from base portion 474. Engaging members 476 define a generally U-shaped slot 478 configured to receive connecting rod 1000 therein. Engaging members 476 are biased radially outward. Each engaging member 476 includes a surface 482 (FIG. 56) configured to engage an inner surface of taper lock head 450 to secure connecting rod 1000 in slot 478, as will be discussed hereinbelow. Surface 482 is tapered, whereby when the taper lock head 450 is in the unlocked position, an inner surface of taper lock head 450 is disengaged (spaced apart) from surface 482. Base portion 474 is generally cylindrical and is configured to slidably engage taper lock head 450.

With particular reference to FIGS. 54 and 56-58, hook housing member 410 defines a pair of opposing V-shaped notches 415. Notches 415 extend from hook member 420 to inner collet portion 470. Notches 415 are opened to slot 478 to aid radial deflection of engaging members 476. Engaging members 476 of inner collet portion 470 are biased radially outward. However, V-shaped notches 415 enable engaging members 476 to move radially inward to securely grip connecting rod 1000 within slot 478.

With reference to FIGS. 59-62, taper lock head 450 is generally cylindrical and defines an opening 452 configured to receive inner collet portion 470 therethrough. Taper lock head 450 defines a pair of diametrically opposing cut out portions 454 configured to accommodate connecting rod 1000 therethrough. In addition, taper lock head 450 further includes lips 456 extending radially outward. Taper lock head 450 defines a bore 458 configured to secure pin 490 therein. Pin 490 is configured to slide within slot 480 (FIGS. 55 and 58) of base portion 474 of inner collet portion 470 to secure sliding movement taper lock head 450 relative to inner collet portion 470.

With reference now to FIGS. 51a and 59, taper lock head 450 is selectively movable along longitudinal axis "B-B" between a locked position and an unlocked position to releasably secure connecting rod 1000 within slot 478 defined by engaging members 476 of inner collet portion 470. In the unlocked position (FIG. 52), the pair of engaging members 476 of inner collet portion 470 is spread apart. In particular, an inner surface of taper lock head 450 is disengaged (spaced apart) from the tapered surface 482 of engaging members 476. In this manner, engaging members 476 of inner collet portion 470 is spaced substantially wider than a diameter of connecting rod 1000 to facilitate insertion of connecting rod 1000 into slot 478 or to facilitate removal of connecting rod 1000 from slot 478. To transition engaging members 476 of inner collet portion 470 from the unlocked position (FIG. 52) to the locked position, taper lock head 450 is slidably moved away from hook portion 420 relative to the inner collet portion 470, such that the inner surface of taper lock head 450 engages surface 482 of engaging member 476, which, in turn, causes engaging members 476 to move toward each other. In this manner, connecting rod 1000 disposed between engaging members 476 is secured within slot 478.

In use, spinal hook 400 is positioned adjacent a desired spinal portion, such that hook member 420 engages the desired spinal portion. Connecting rod 1000 is then placed in slot 478 of inner collet portion 470. At this time, inner collet portion 470 may be transitioned to the locked position to completely secure connecting rod 1000 within slot 478 by sliding taper lock head 450 away from hook member 420.

While spinal hooks 100, 200, 300, 400 have been described to transition between a locked state in which connecting rod 1000 is secured with spinal hooks 100, 200, 300, 400 and an unlocked state in which connecting rod 1000 is releasable from spinal hooks 100, 200, 300, 400, spinal hooks 100, 200, 300, 400 may partially lock connecting rod 1000 therein. Partially locking connecting rod 1000 enables connecting rod 1000 to slidably engage spinal hooks 100, 200, 300, 400. In this manner, the clinician may slide spinal hooks 100, 200, 300, 400 on connecting rod 1000.

It is also envisioned that spinal hooks 100, 200, 300, 300 may be used with other surgical instruments such as, e.g., a rod reduction device, configured to reduce a rod into position in a rod receiving slot in a head of a bone screw with a controlled, measured action. Reference may be made to U.S. Pat. No. 7,931,654, filed on Sep. 26, 2006, and U.S. Patent Application Publication No. 2009-0018593, filed on Jul. 13, 2007, the entire contents of each of which are incorporated herein by reference, for a detailed discussion of the construction and operation of a rod reduction device.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A spinal hook comprising:
a hook housing member including a head portion and a blade portion, wherein the head portion and the blade portion of the hook housing member are monolithically formed; and
an inner collet slidably associated with the hook housing member, the inner collet including a pair of engaging portions defining a first slot therebetween, the first slot configured to receive a connecting rod therein, wherein the inner collet is transitionable between an unlocked state in which the pair of engaging portions are spaced apart to receive the connecting rod within the first slot and a locked state in which the pair of engaging portions secure the connecting rod within the first slot.

2. The spinal hook according to claim 1, wherein the inner collet includes a second slot and the head portion of the hook housing member includes a pin configured to slidably engage the second slot of the inner collet.

3. The spinal hook according to claim 1, wherein the inner collet includes a slit extending along a length thereof to facilitate radial deflection of the inner collet.

4. The spinal hook according to claim 3, further comprising a retaining member configured to be disposed in a recess defined in the inner collet such that the retaining member causes the inner collet to expand radially outward thereby enabling a portion of the inner collet to be selectively positionable within the head of the hook housing member.

5. The spinal hook according to claim 3, wherein at least a portion of the inner collet is slidably disposed within the head portion of the hook housing member.

6. The spinal hook according to claim 3, wherein the slit has an opening leading into the first slot.

7. The spinal hook according to claim 3, wherein each of the pair of engaging portions includes a surface configured to engage an inner surface of the head portion to transition the inner collet between the locked and unlocked states.

8. The spinal hook according to claim 7, wherein the surface is tapered such that in the unlocked state, the surface is spaced apart from the inner surface of the head portion.

9. A spinal hook comprising:
a head portion defining an aperture; and
a hook housing portion including a hook member and an inner collet portion having a base portion and engaging members extending from the base portion, the hook member and the inner collet portion being monolithically formed, the inner collet portion defining a first slot configured to receive a connecting rod between the engaging members, wherein the hook housing portion is movable relative to the head portion between a unlocked position in which the engaging members are disengaged from a connecting rod disposed in the first slot of the inner collet portion and a locked position in which the engaging members secure a connecting rod disposed in the first slot.

10. The spinal hook according to claim 9, wherein each engaging member includes a surface configured to engage an inner surface of the head portion.

11. The spinal hook according to claim 10, wherein the surface of the engaging member is tapered such that when the head portion is in the unlocked position, the surface of the engaging member is disengaged from the inner surface of the head portion.

12. The spinal hook according to claim 9, wherein the base portion of the inner collet portion has a generally cylindrical shape and is configured to slidably engage the head portion.

13. The spinal hook according to claim 9, wherein the hook housing portion defines a notch tapered along a length of the hook housing portion.

14. The spinal hook according to claim 13, wherein the notch is open to the first slot to facilitate radial deflection of the engaging members.

15. The spinal hook according to claim 9, wherein the head portion defines a bore configured to receive a pin slidably received within a second slot defined in the base portion of the inner collet portion.

16. The spinal hook according to claim 9, wherein the engaging members are biased radially outward.

17. The spinal hook according to claim 9, wherein the first slot is U-shaped.

* * * * *